United States Patent [19]
Hussman

[11] Patent Number: 5,590,655
[45] Date of Patent: Jan. 7, 1997

[54] FRAMELESS LASER GUIDED STEREOTACTIC LOCALIZATION SYSTEM

[76] Inventor: Karl L. Hussman, 1900 E. Ocean Blvd., #318, Long Beach, Calif. 90802

[21] Appl. No.: 196,842

[22] Filed: Dec. 15, 1994

Related U.S. Application Data

[63] Continuation-in-part of Ser. No. 124,690, Sep. 20, 1993, Pat. No. 5,437,280, Ser. No. 139,934, Oct. 20, 1993, abandoned, and Ser. No. 172,088, Dec. 22, 1993, abandoned.

[51] Int. Cl.$^6$ ............................................. A61B 6/00
[52] U.S. Cl. .................... 128/653.1; 606/130; 128/653.2
[58] Field of Search ...................... 606/130; 128/653.1, 128/653.2, 654, 754

[56] References Cited

U.S. PATENT DOCUMENTS

| | | | |
|---|---|---|---|
| 4,583,538 | 4/1986 | Onik | 606/130 |
| 4,651,732 | 3/1987 | Frederick | 606/130 |
| 5,221,283 | 6/1993 | Chang | 606/130 |

*Primary Examiner*—Ruth S. Smith
*Attorney, Agent, or Firm*—Timothy T. Tyson; Freilich, Hornbaker & Rosen

[57] ABSTRACT

A lesion localization system is disclosed which employs imaging visible members (926, 928), and manifested sets of imaging space coordinates to define a retrograde point (1004) that is colinear with a lesion (940) and a selected entry point (946) thereto. Retrograde and antegrade lasers (1014, 1015) are employed to use the retrograde point in guidance of a medical instrument to the lesion. The localization system avoids mechanical calibration of stereotactic frames and is simpler to operate.

19 Claims, 25 Drawing Sheets

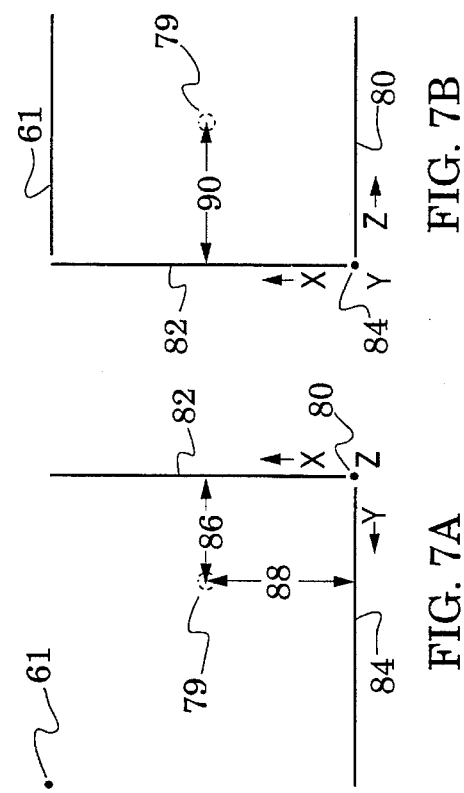
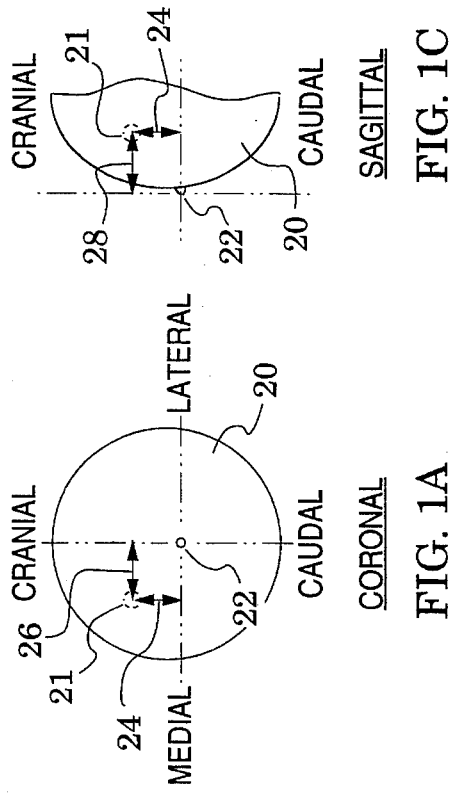
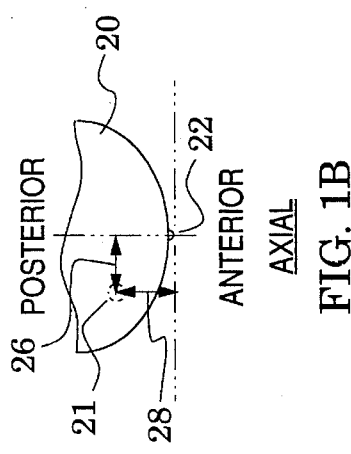

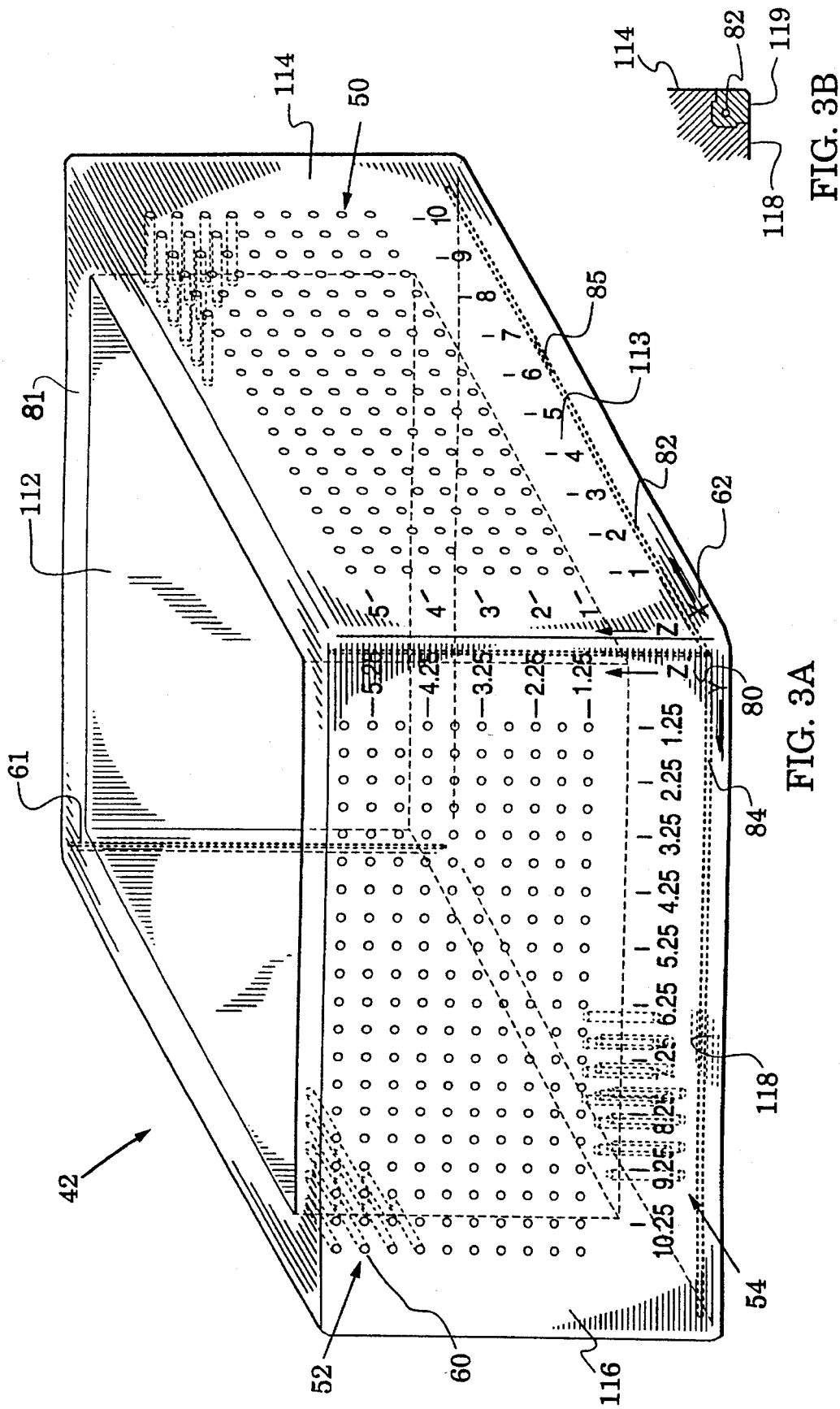

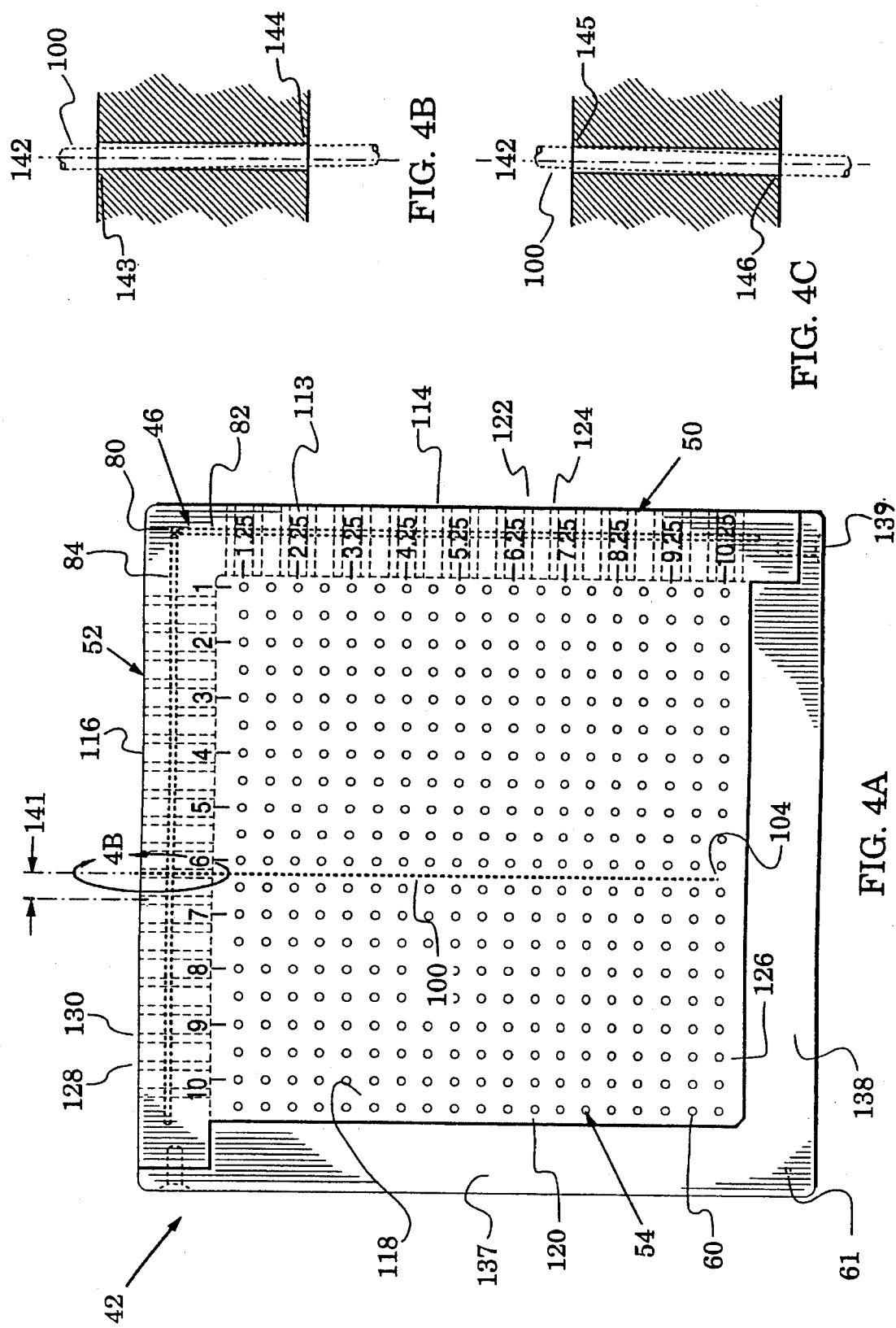

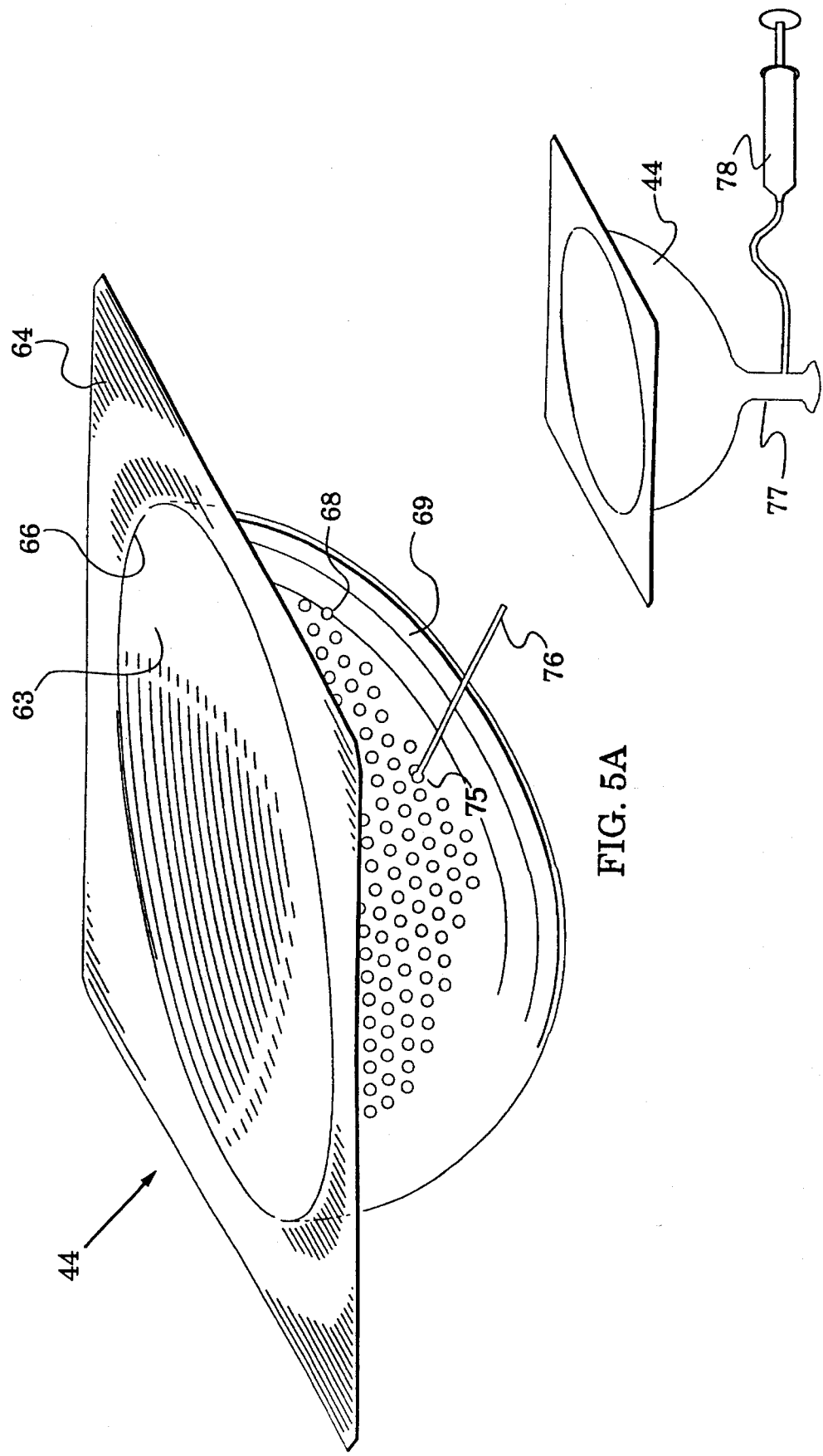

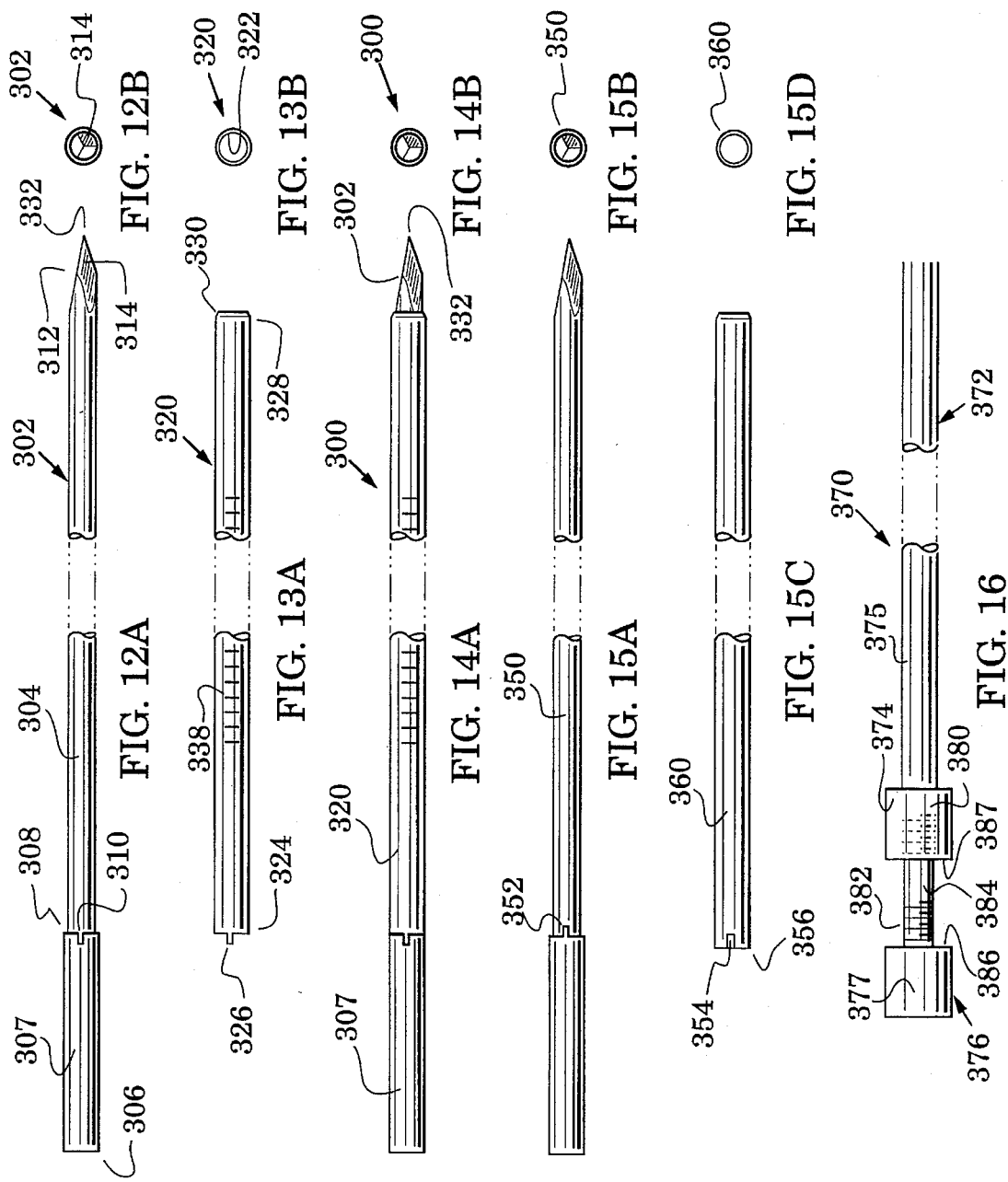

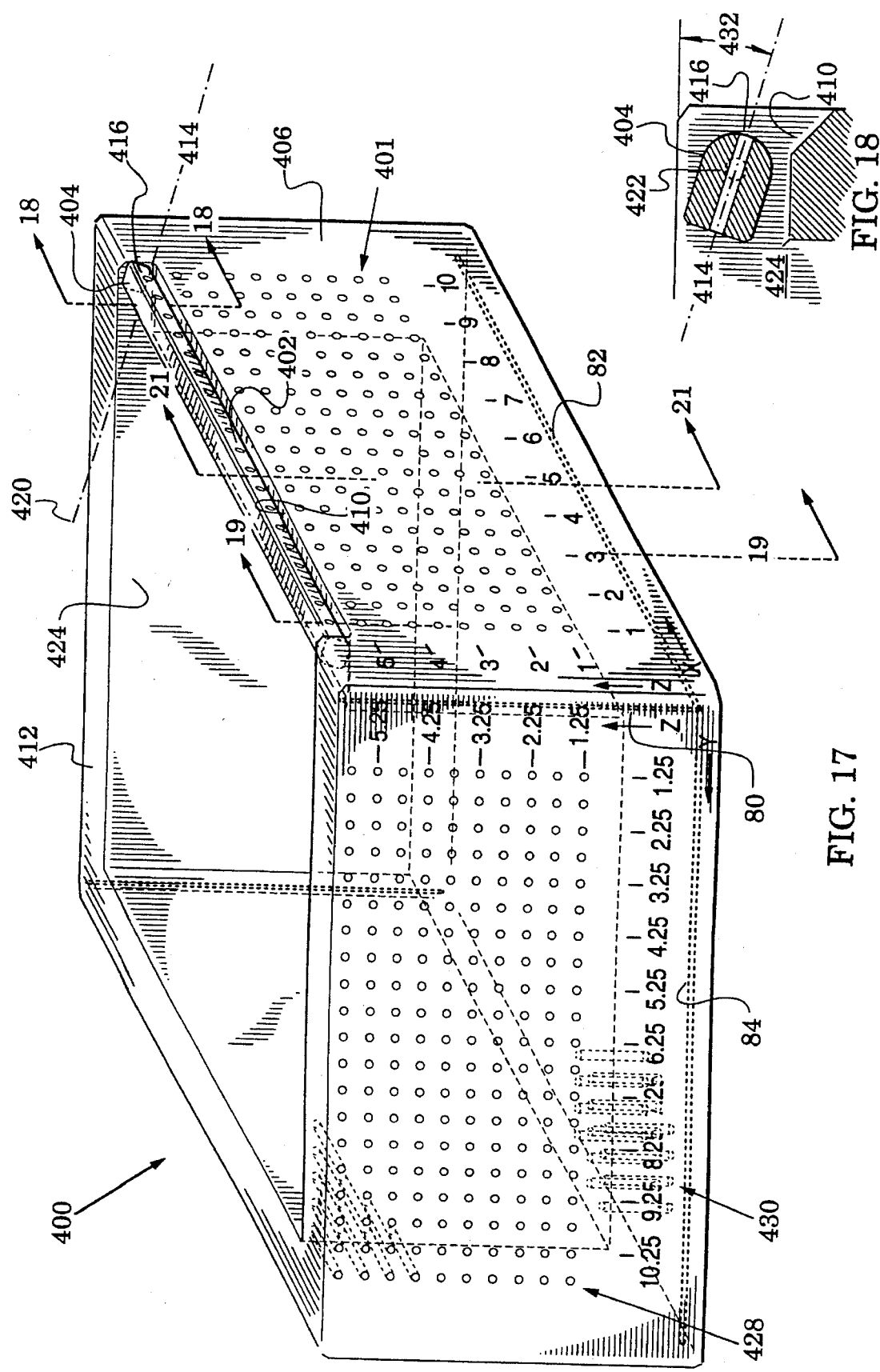

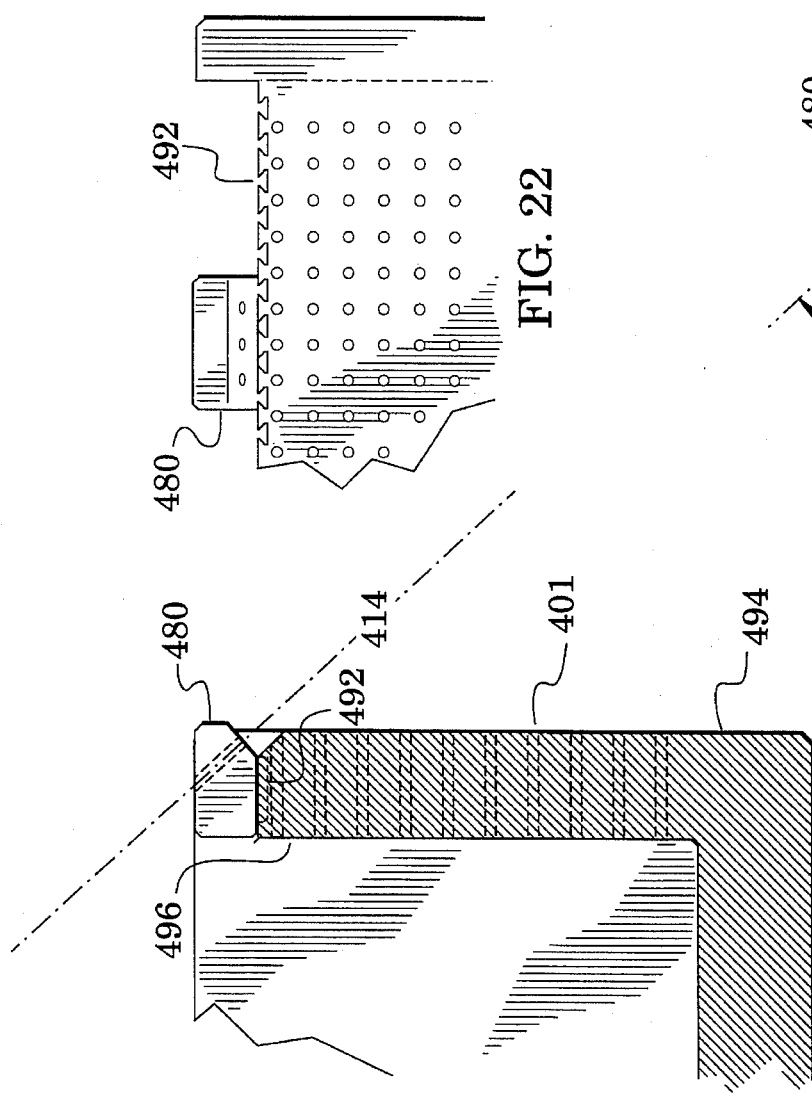
FIG. 22
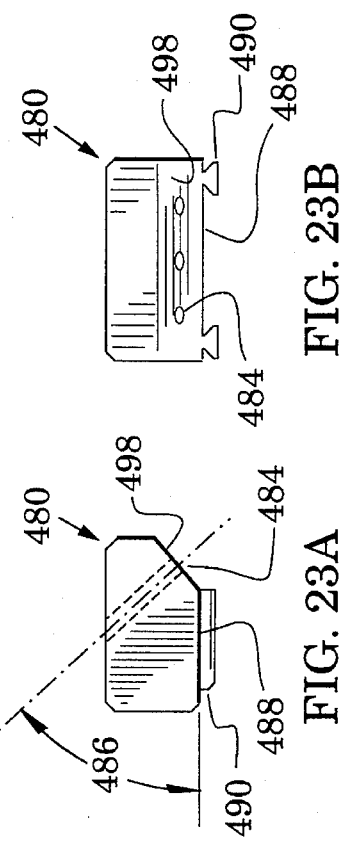
FIG. 23A
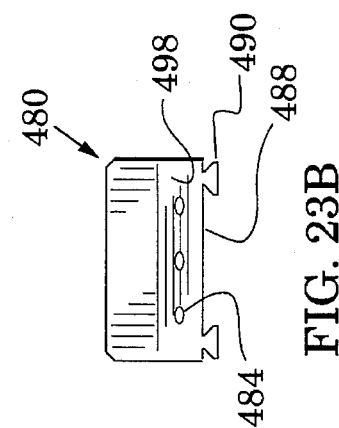
FIG. 23B
FIG. 21

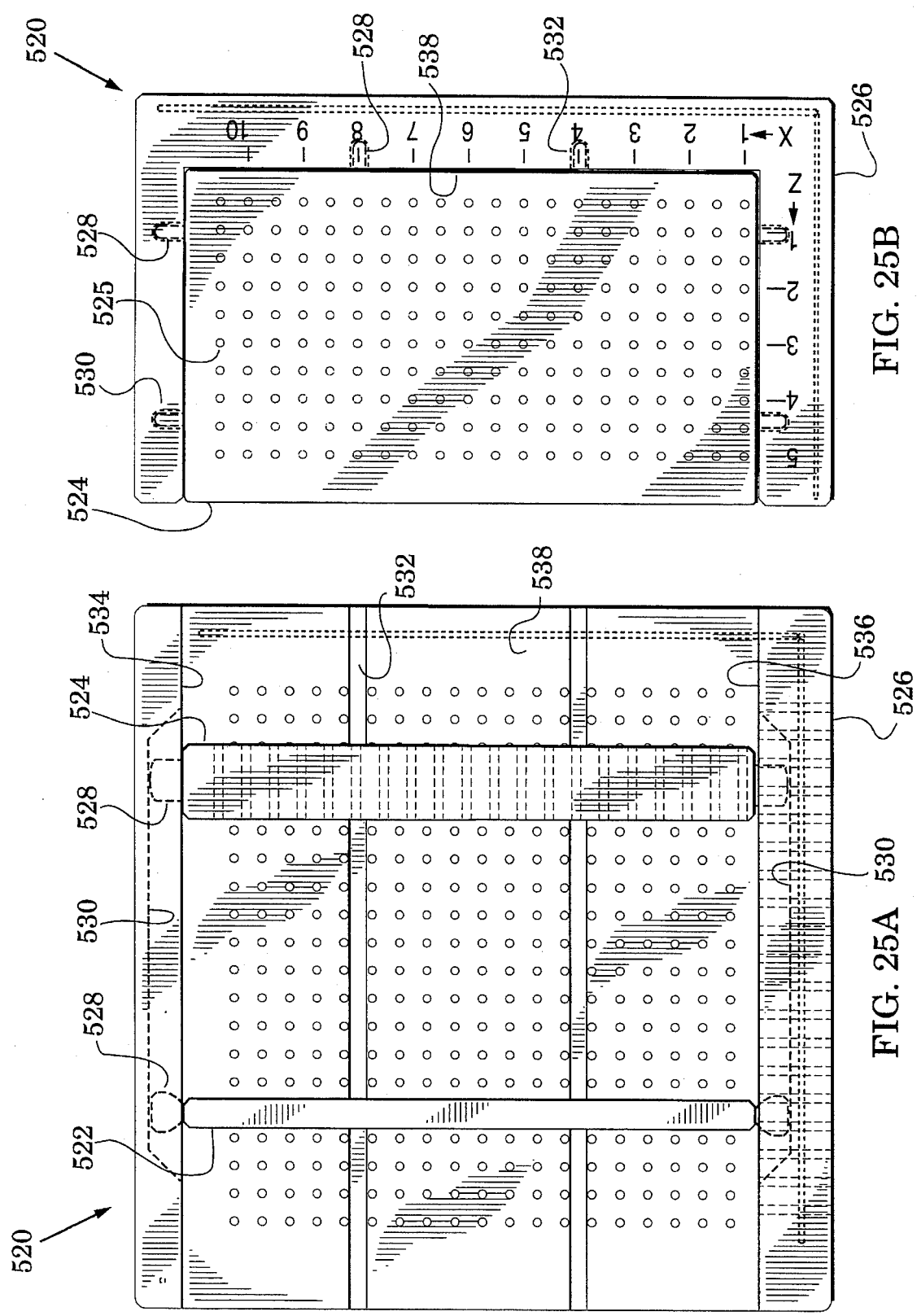

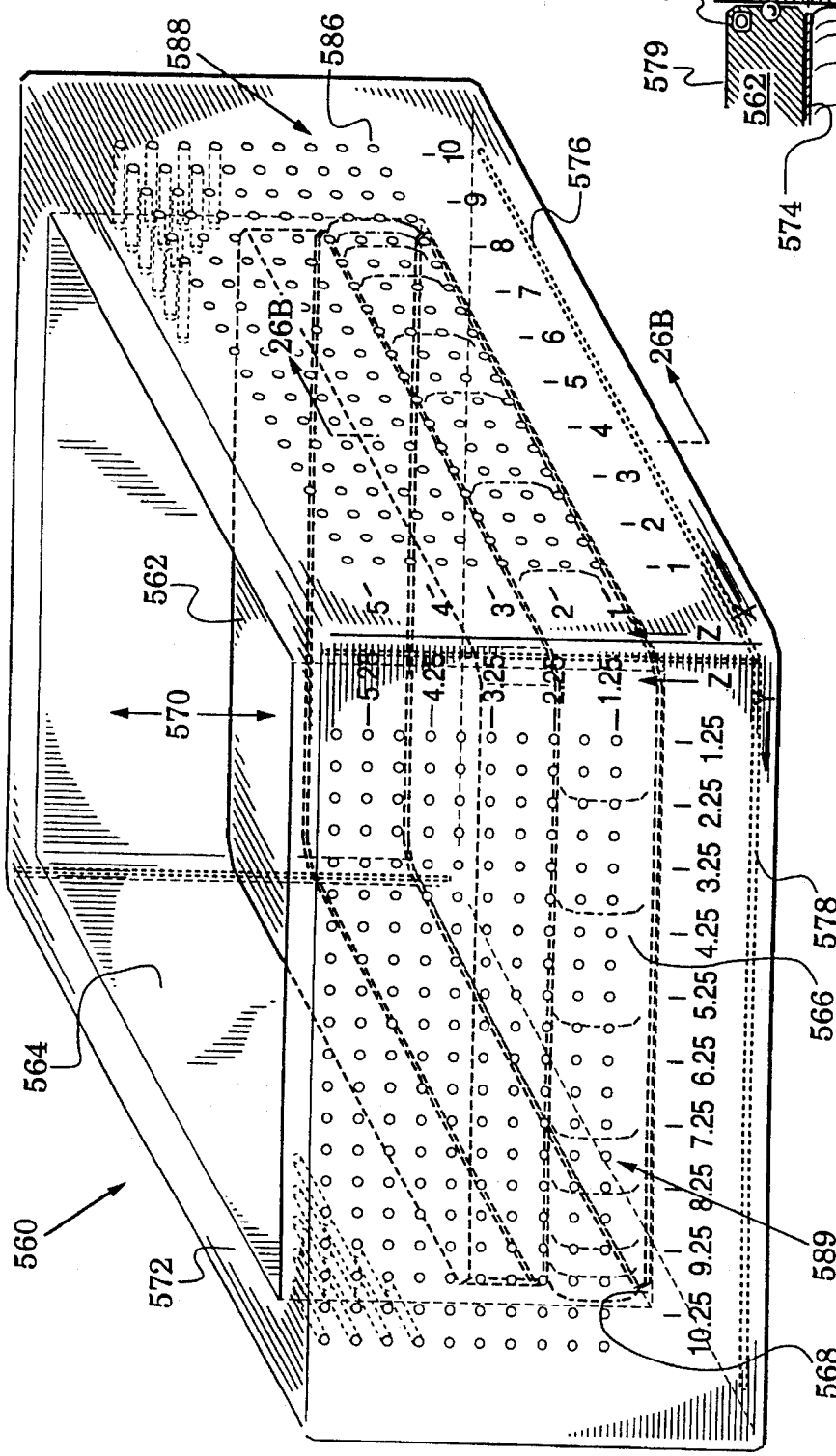
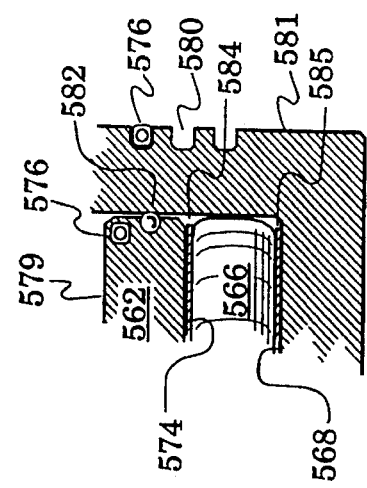
FIG. 26A
FIG. 26B

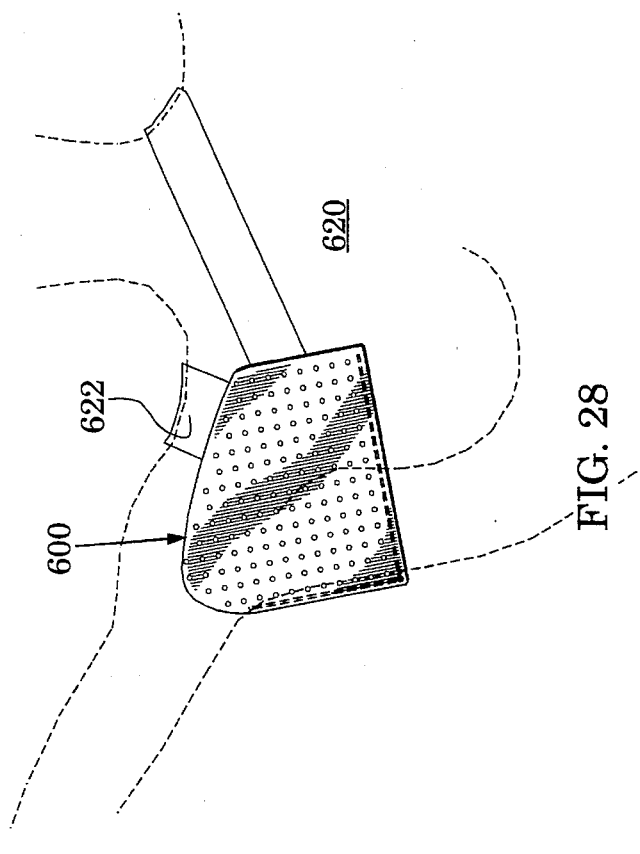
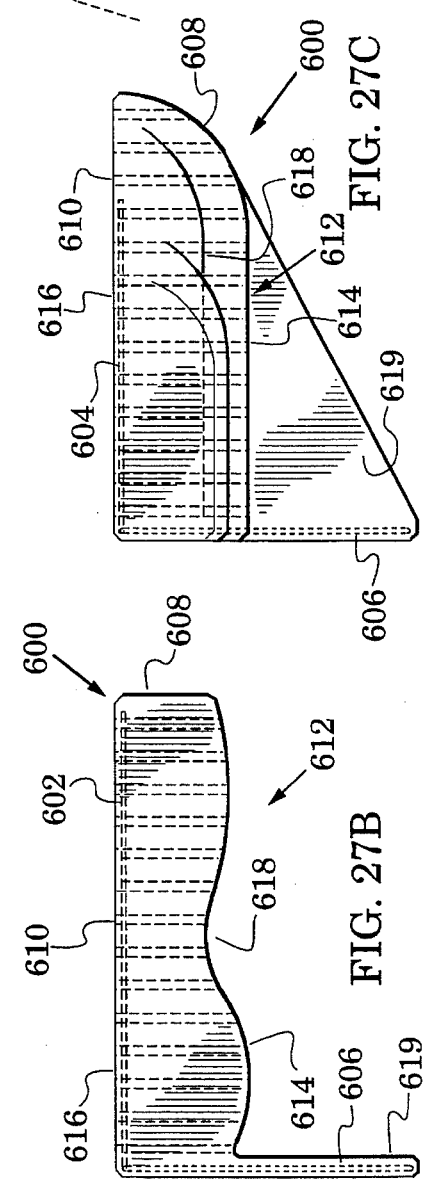
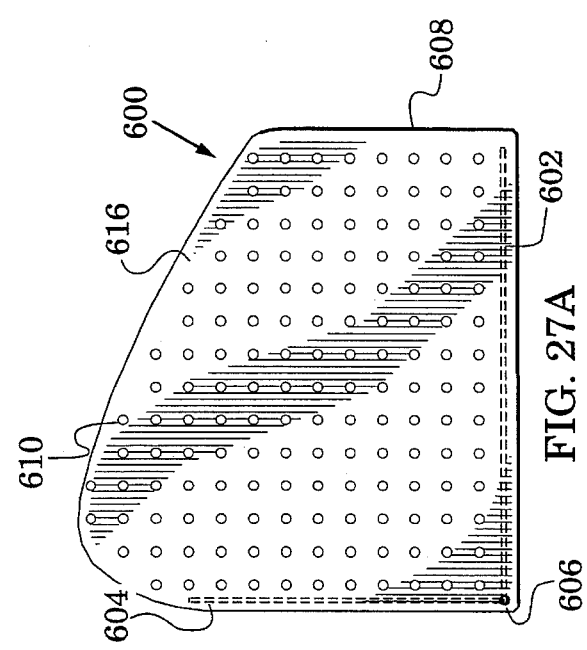

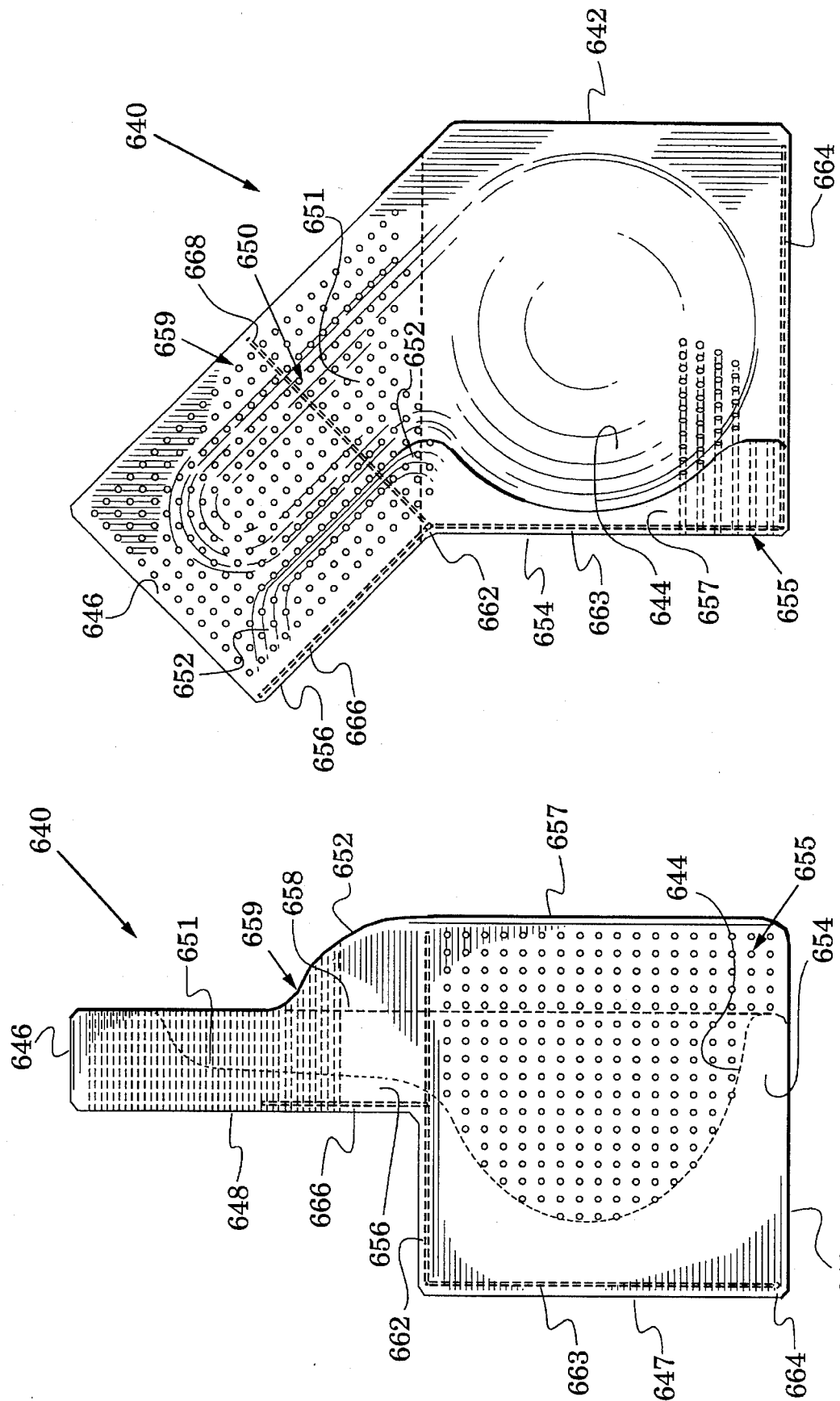

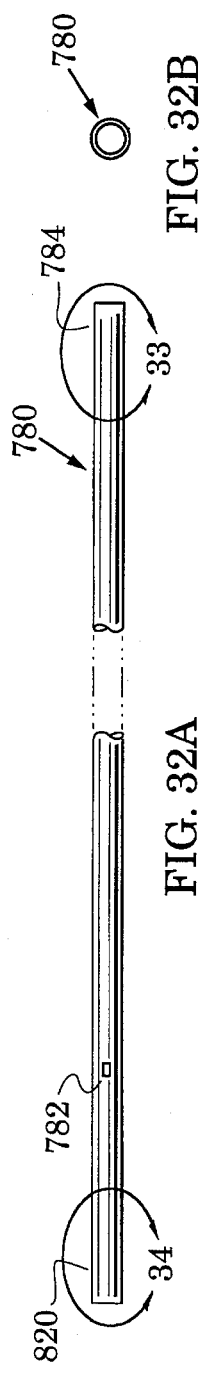

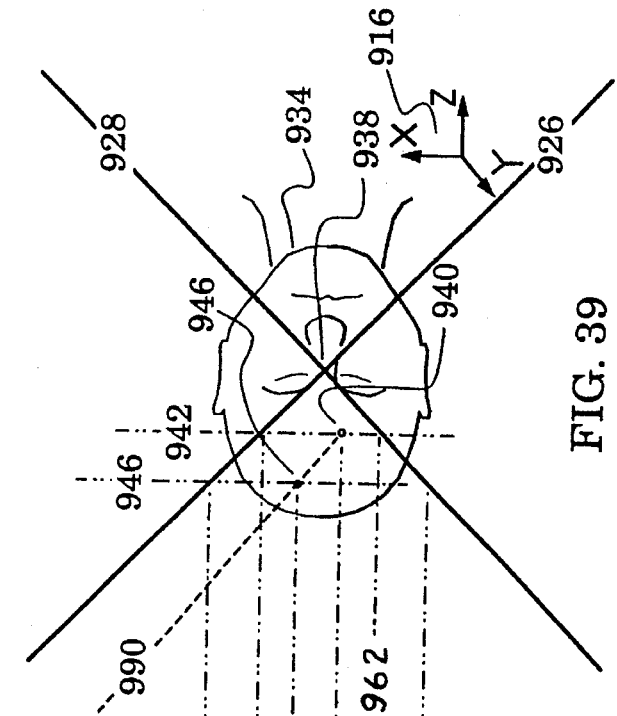
FIG. 39
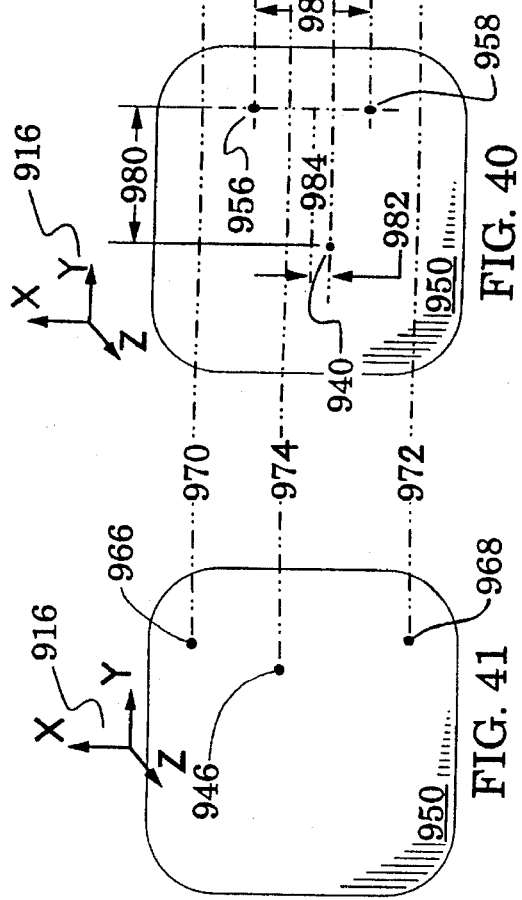
FIG. 40
FIG. 41
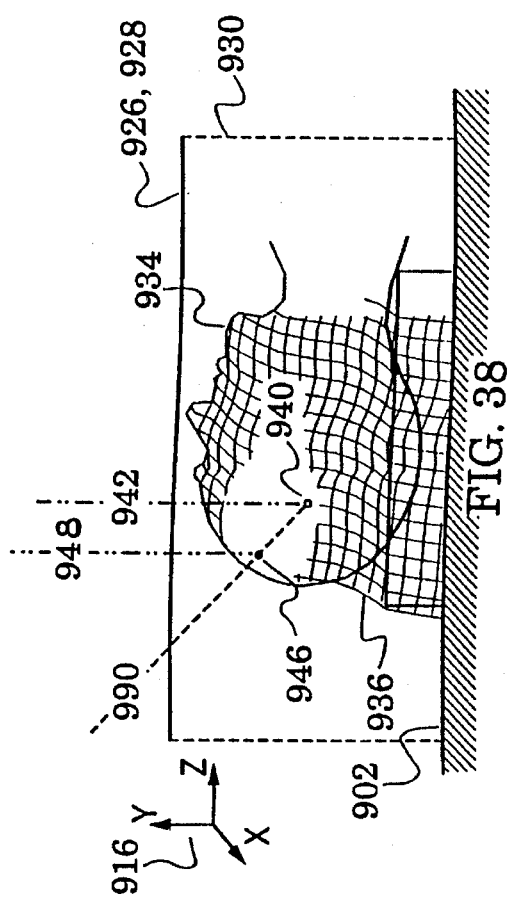
FIG. 38

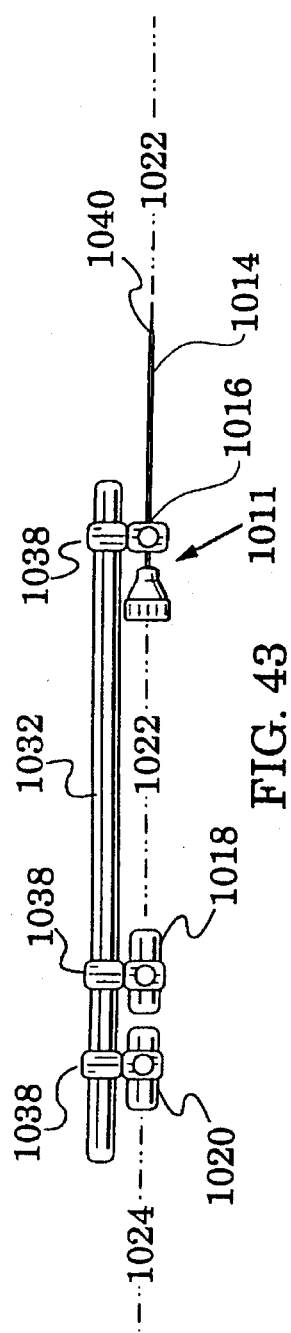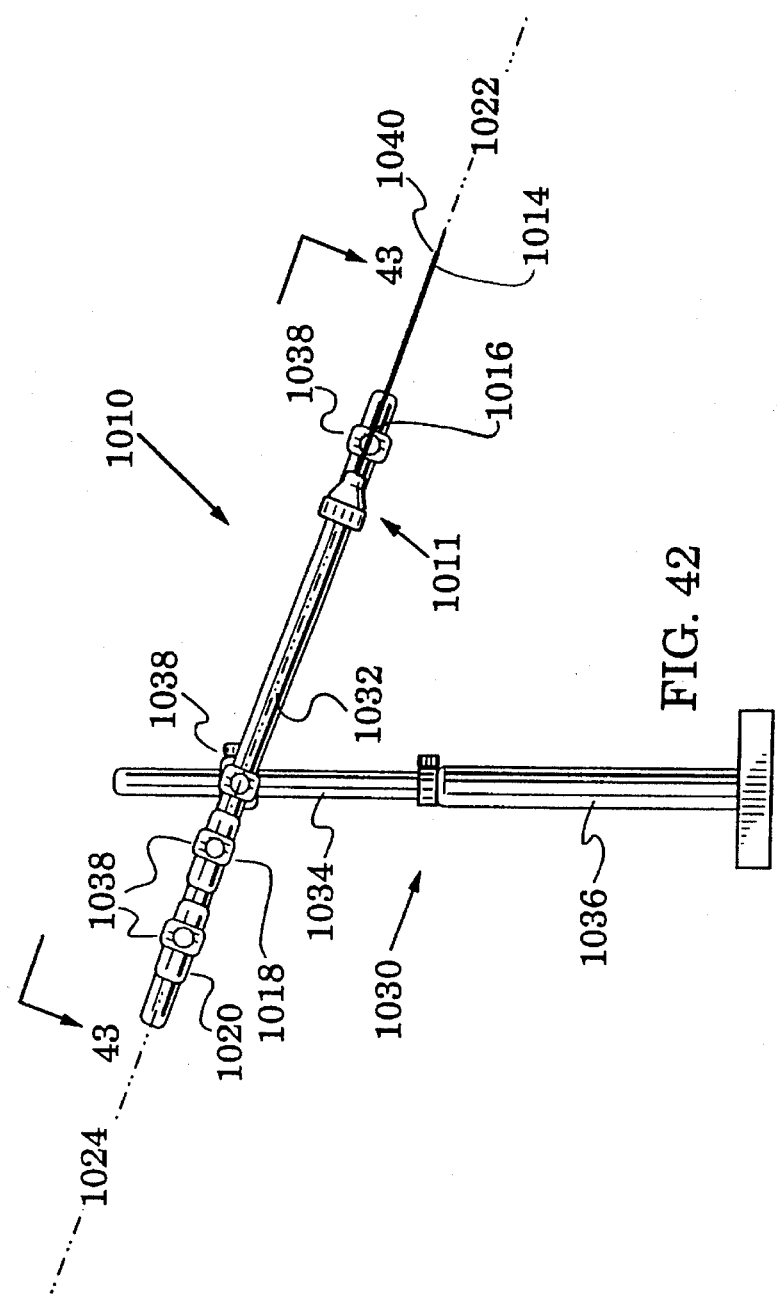
FIG. 43
FIG. 42

FRAMELESS LASER GUIDED STEREOTACTIC LOCALIZATION SYSTEM

CROSS REFERENCES TO RELATED APPLICATIONS

This is a continuation-in-part of application Ser. No. 08/124,690 filed Sep. 20, 1993, now U.S. Pat. No. 5,437,280 application Ser. No. 08/139,934 filed Oct. 20, 1993 abandoned and application Ser. No. 08/172,088 filed Dec. 22, 1993, abandoned the disclosures of which arc hereby incorporated by reference.

FIELD OF THE INVENTION

The present invention relates generally to lesion localization.

BACKGROUND OF THE INVENTION

Breast cancer is the leading cause of death from cancer among women in the western world and the leading cause of death in general among persons 35 to 55 years of age. Imaging modalities for detection of breast lesions include X-ray mammography, sonography, thermography, computed tomography, angiography and magnetic resonance imaging (MRI) which are copiously described in the literature.

MRI literature references include MR Mammography, Kaiser, Werner A., Springer-Verlag, Berlin Heidelberg, 1993; Kaiser, Werner A., MRM promises earlier breast cancer diagnosis, Diagnostic Imaging, September, 1992; Liu, Haiying, et al., Fat Suppression with an Optimized Adiabatic Excitation Pulse, Proceedings of the Twelfth Annual Scientific Meeting of the Society of Magnetic Resonance in Medicine, 1993, 3:1188; Hajek, Paul, et al., Localization Grid for MR-guided Biopsy, Radiology, 1987; Harms, S. E., MR Imaging of the Breast, JMRI, January/February, 1993; Heywang-Kobrunner, Sylvia, Nonmammographic Breast Imaging Techniques, Current Opinion in Radiology, 1992; Harms, S. E., et al., MR Imaging of the Breast with Rotating Delivery of Excitation Off Resonance, Radiology, 1993 and Liu, H., et al., Biplanar Gradient Coil Imaging (abstract), JMRI, 1993.

X-ray localization literature references include Svane, G., Stereotaxic Technique for Preoperative Marking of Non-Palpable Breast Lesions, Acta Radiologica Diagnosis, 1983; Langlois, S. L., et al., Carbon Localization of Impalpable Mammographic Abnormalities, Australasian Radiology, August, 1991.

Stereotaxic localization literature references include Cosman, Eric, et al., Combined Use of a New Target-Centered Arc System, Proceedings of the Meeting of the American Society for Stereotactic and Functional Neurosurgery, Montreal 1987; Giorgi, C., et al., Three-dimensional Reconstruction of Neuroradiological Data, applied Neurophysiology, 1987; and Derosier, C., MR and Stereotaxis, J. Neuroradiol, 1991.

Breast cancer pathology literature references include Lagois, M. D., et al., The Concept and Implications of Multicentricity in Breast Carcinoma, Pathology Annual, Appleton-Century-Crofts, New York, 1981.

Interstitial laser photocoagulation literature references include Castro, Dan, Metastatic Head and Neck Malignancy Treated Using MRI Guided Interstitial Laser Phototherapy, Laryngoscope 102, January, 1992; Steger, A. C., et al., Interstitial Laser Hyperthermia, Br Medical Journal, 1989, 299 and Bown, S. G., Minimally Invasive Therapy in Breast Cancer (abstract), JMRI, 1993.

Drill biopsy literature references include Ahlstom, K. Hakan, CT-guided Bone Biopsy, Radiology, 1993 and Meyerowitz, Basil R., Drill Biopsy Confirmation, Arch Surg, volume 111, July, 1976.

Literature references more specifically pertaining to MRI breast localization techniques include Hussman, Karl, et al., MR Mammographic Localization Work in Progress, Radiology, 1993, 189 (p): 915; Heywang-Kobrunner, S. H., MRI of Breast Disease, Presented at the Twelfth Annual Scientific Meeting of the Society of Magnetic Imaging in Medicine, 1993 and Schnall, M. D., et al., A System for MR Guided Stereotactic Breast Biopsies and Interventions, Proceedings of the Twelfth Annual Scientific Meeting of the Society of Magnetic Resonance in Medicine, 1993, 1:163. A pertinent reference pertaining to X-ray mammographic localization utilizing a bore array is Prejean, J., et al., How to Construct and Use a Low-Cost Precision Device for Performing Breast Biopsy, Radiology, 1993, 189 (p): 407. The disclosures of the above cited references are hereby incorporated by reference and liberally drawn from for this background section.

MRI can be realized because atoms with an odd number of protons or neutrons possess an intrinsic rotation or "spin" that, for clarity, may be likened to the spinning of a top. The atomic nucleus also carries an electric charge, and the combination of spin and charge leads to the generation of a magnetic field around the particle. The nucleus, then, represents a magnetic dipole whose axis is directed parallel to the axis of spin.

In the absence of an applied external magnetic field, the orientations of the proton spin axes are distributed statistically in space, so the magnetic dipoles cancel out in terms of their external effect. When a patient is placed into a magnetic field, the magnetic moments become oriented either parallel or antiparallel to the external field. Each state has a different energy level, the parallel alignment being the more favorable state in terms of energy. To alter these different energy states, the energy difference must either be added to or absorbed from the system from the outside. This can be accomplished by the application of an electromagnetic pulse at the magnetic resonance (MR) frequency or "Larmor frequency". In a magnetic field of 1 Tesla, for example, the Larmor frequency is 42 MHz.

The applied radio frequency pulse tilts the spin axis of the protons out of alignment by an angle that depends on the amplitude and duration of the transmitted electromagnetic pulse. A 90° pulse is one that tilts the magnetization vector from the z axis to the xy plane, while a 180° pulse causes a complete inversion of the magnetization vector.

After the excitation pulse has passed, relaxation commences as the nuclei return to their original states. This realignment process is characterized by a relaxation time T1 and corresponds to the motion of an electric charge in a magnetic field. As a result, the relaxation process causes the emission of an electromagnetic signal (the MR signal) from the nuclei that can be detected with special antennas (coils).

When the resonance frequency is applied to the sample as a 90° pulse, the pulse not only tilts the magnetic moment 90° but also tends to align the spin axes in the direction of the rf pulse. The angle of the spin axes is called the "phase". When the rf pulse ceases, the individual spins immediately begin to go out of phase. This "dephasing" process is called spin-spin relaxation and is characterized by a T2 relaxation time. The spin-lattice or T1 relaxation time describes the return of the magnetic moment to alignment with the external magnetic field. Both processes occur simultaneously in the same nucleus. Characteristic T1 values in biologic tissues range from 0.5 to 2 seconds and T2 values from 10 to 200 milliseconds.

By modifying the amplitude and duration of the applied rf pulses, an investigator can manipulate the alignment of the nuclear spins in varying degrees and for varying lengths of time. Accordingly, the MR signals generated by the tissue relaxation process vary greatly depending on the type of excitation pulses that are applied. The basic pulse sequences in clinical use include spin-echo, inversion recovery, gradient echo and fat suppression. Specialized pulse sequences under these general types include FLASH, FISP, RODEO and SNOMAN.

Image plane selection (slice selection) is accomplished by superimposing a linear gradient field upon a static magnetic field. Because the gradient field increases linearly in one direction, e.g., along the z axis, there is only one site at which the resonance or Larmor frequency condition is met. The bandwidth of an applied rf pulse and the steepness of the gradient determine the thickness of the tissue slice from which MR signals emanate. When two additional gradient fields are applied in the x and y directions, frequency or phase information can be assigned to different points within the selected plane.

A complete pulse sequence yields a raw-data image called a hologram. A 2-dimensional Fourier transform is applied to the raw data to construct the final image. Through the switching of magnetic gradients, sectional images can be constructed on a coronal, axial or sagittal plane or in any oblique orientation desired (coronal, axial and sagittal planes are respectively those dividing the frame into front and back portions, those dividing the frame into right and left portions and those dividing the frame into upper and lower portions).

Components of an MR unit include a primary magnet, shim coils whose current supply is computer controlled to produce the desired field homogeneity, gradient coils to generate linear gradient fields, an rf coil for transmitting the rf pulses and receiving the MR signals (the signals may be received through the transmitting coil or a separate receiving coil), a computer for control of data acquisition, imaging parameters, and analysis and data storage media.

The rf excitation signal and the MR signal emitted by relaxing nuclear spins are respectively transmitted and received with rf coils types that include surface coils, whole-volume coils (in solenoid, saddle and birdcage configurations), partial-volume coils, intracavitary coils and coil arrays.

Breast coils are typically whole-volume solenoids used both for transmission and receiving. Such coils are especially suited for imaging frame regions that are perpendicular to the magnet aperture, e.g., breasts, fingers. They include square 4 pole resonators that can be inserted over the breast during imaging and Helmholtz pair resonators. Pairs of breast coils are often coupled to allow imaging of both breasts, e.g., see Model QBC-17 Phased Array Breast Coil, MRI Devices Corporation, 1900 Pewaukee Road, Waukesha, Wis.

The MR signal intensity varies exponentially with T1 and T2. Thus, a substance that alters the tissue relaxation times can be a potent image contrast enhancer. Gadolinium—diethylene triamine—pentaacetic acid (Gd-DTPA) is particularly suitable for producing contrast enhancement. Enhancement following injection seems to correlate with the vascularization of the lesion and the intense MR signal enhancement in carcinomas may be due to their increased vascular density.

Dynamic imaging involves repetitive imaging of the same slices before and after injection of Gd-DPTA. Dynamic, contrast-enhanced MR imaging has been found to be especially effective in differentiating benign from malignant lesions. MR signal increases (typically within the first minute after injection) can help differentiate carcinoma from benign breast lesions such as fibroadenoma, proliferative mastopathy, cysts, scars and mastopathies.

Numerous investigations and tests have demonstrated the high sensitivity (proportion of people having a disease that are so identified by a test) and specificity (proportion of people free of a disease that are so identified by a test) of MR imaging and its ability to detect even small cancers, e.g., 3–5 millimeters. However, successful imaging of breast lesions must be accompanied by effective guidance of medical instruments to the lesion site to facilitate diagnosis and treatment.

Accurate guidance is especially difficult in breasts because they lack rigid structure as, for example, in the cranium and can assume numerous configurations. FIGS. 1A, 1B and 1C are respectively front, top and side views of a breast 20 and illustrate how the location of a breast lesion 21 is typically described in relation to a coordinate system centered on the breast nipple 22. In these views, the lesion 21 exhibits cranial spacing 24, medial spacing 26 and posterior spacing 28 from the nipple 21. However, it is apparent that if the breast 20 were allowed to assume a configuration different from that of FIGS. 1, these spacings would no longer accurately describe the lesion location. Thus, imaging and localization procedures are preferably completed without disturbing the breast position therebetween so that the imaging spacings used for localization are not corrupted.

Non-invasive localization or guidance techniques include measurement of the spacing between the lesion and the nipple and between the lesion and the overlying skin surface and transposition of the measurements to the breast surface where the calculated site is marked as a guide for a surgeon. Because of the considerations described above, non-invasive techniques generally permit only approximate guidance.

Invasive localization techniques often include apparatus for reducing breast movement. For example, perforated compression plates are described in Svane, Schnall, Heywang-Kobrunner and Prejean in the above incorporated references. Localization using an MR visible coordinate system is described by Hussman, Heywang-Kobrunner and Schnall in the above mentioned references. Localization using bores which guide and stabilize the needle tip is described by Prejean and Hussman in the above mentioned references. Instructions (including a video tape) for constructing a needle guide-hole grid for localization of non-palpable mammographic lesions have been prepared by Prejean, J., et al. Schnall and Hewang-Kobrunner demonstrated compression grid localizers using guiding bore arrays at the 79th Scientific Assembly and Annual Meeting of the Radiological Society of North America in Chicago, Nov. 28–Dec. 3, 1993. Gd-DTPA filled polyethylene tubes arranged in a grid and taped to an abdomen as a localization aid are described in Hajek in the above incorporated references.

Invasive treatment techniques include the insertion of a carbon trail leading to the lesion vicinity with a carbon trail injector as described in Svane and Langlois in the above incorporated references. The carbon trail serves as a marker to guide a surgeon to the lesion. Hook-wires are inserted to the lesion vicinity for the same purpose. They are typically removed during surgery. Introducing a fiber optic to the lesion vicinity for treatment with laser energy is described in Bown and Steger in the above incorporated references (interstitial laser photocoagulation or ILP in Bown; interstitial laser hyperthermia in Steger). In these treatment techniques, the laser fiber is typically passed through a thin needle to the lesion site.

Preferably, laser therapy is performed with the breast in a relaxed position to avoid forcing (as in compression techniques) a lesion proximate to the skin surface rendering it inaccessible to laser therapy because of the risk of skin necrosis.

Other well known invasive procedures include the introduction of a needle for aspiration biopsy, a rotex screw biopsy needle within a cannula and a trocar within a cannula. Meyerowitz describes the use of a high speed drill for drill biopsy of breast lesions. Hussman suggests its use for approaching breast lesions without substantial breast compression prior to drill biopsy of the lesion itself. In general, the goal of successful localization is the guidance of a medical instrument tip to the lesion site determined by imaging.

Because of the large magnetic fiends involved in MR imaging, it is highly desirable that only nonferromagnetic materials be introduced within the magnetic fields. In addition, some materials can produce imaging artifacts (other sources of imaging artifacts include patient movement, heart movements, and chemical shifts due to resonance frequency difference of water and fat protons). Materials that do not exhibit nuclei relaxation will not appear on the MR image. On the other hand, if it is desired that a structure appear on the MR image, the material of that structure should exhibit nuclei relaxation.

Materials that do not cause imaging artifacts nor appear on the MR image shall hereinafter be called MR transparent while materials that are intended to appear on the MR image shall hereinafter be referred to as MR signal-producing. An example of an MR transparent material is polycarbonate. An example of an MR signal-producing material is Gd-DTPA contained in an MR transparent material. Similar terminology will be employed when discussing other imaging modalities, e.g., nuclear medicine, ultrasound and X-ray mammography (including computed tomography).

The term stereotactic arises from stereo, the Greek word for three-dimensional, and either taxic, the Greek word for system or arrangement, or the Latin verb, tactus, meaning to touch. In medical practice it has come to mean the use of geometrically-determined vectors to position instruments, e.g., probes, electrodes, biopsy cannulas and the like, in precise three dimensional space. Stereotactic systems are described in Zinreich, S. J., et al., Frameless Stereotaxic Integration of CT Imaging Data: Accuracy and Initial Applications, Radiology, 1993; 188: 735–742. Lasers are often used in medical instrument alignment and positioning, e.g., TOME-A-LINE/CT positioners manufactured by Gammex Lasers™, Milwaukee, Wis.

SUMMARY OF THE INVENTION

The present invention is directed to methods and apparatus for localization of lesions identified in a patient via an imaging modality.

Methods in accordance with the invention are characterized by the steps of establishing an imaging space coordinate system, indicating a selected patient entry point with an imaging visible marker, imaging the lesion and the marker to determine the imaging space coordinates thereof, determining the intersection of a line defined by the entry point coordinates and the lesion coordinates and a retrograde point wherein the entry point is between the retrograde point and the lesion, and utilizing a retrograde laser coaxial with both the line and a medical instrument to guide the instrument antegrade along the line by illuminating the retrograde point.

In a preferred embodiment, the imaging step includes the steps of disposing two intersecting imaging visible members in a spaced relationship with the lesion and entry point and employing the image of the members and the spaced relationship to geometrically determine the coordinates of each.

In accordance with a feature of the invention, a target point-entry point line is determined with the aid of angled, imaging visible fiduciary members.

In accordance with another feature of the invention, a retrograde point is established as the intersection of the target point-entry point line with a manifested set of imaging space coordinate points.

In accordance with another feature of the invention, the retrograde point is utilized to guide an instrument tip to the lesion.

In accordance with another feature of the invention, the fiduciary members are used to translate spatial relationships found with the imaging modality to the imaging space coordinate system.

BRIEF DESCRIPTION OF DRAWINGS

FIGS. 1A, 1B and 1C illustrate medical coordinates relative to a breast;

FIG. 3A is an isometric view of the frame in the localizer of FIG. 2;

FIG. 3B is a sectional view illustrating removable lumens in the frame of FIG. 3A;

FIG. 4A is a bottom plan view of the localizer of FIG. 2 including removable walls;

FIG. 4B is a view of structure within the curved line 4B—4B of FIG. 4A;

FIG. 4C is a view similar to FIG. 4B;

FIG. 5A is an isometric view of the cup in the localizer of FIG. 2;

FIG. 5B is a reduced view of FIG. 5A including suction structure;

FIG. 6 is a schematic view of a breast volume measurement method;

FIG. 7A is an MR computer display of an imaged lesion and coordinate system;

FIG. 7B is another MR computer display of an imaged lesion and coordinate system;

FIG. 12A is a side view of a preferred trocar embodiment for use with the preferred localizer embodiments;

FIG. 12B is an end view of the trocar of FIG. 12A;

FIG. 13A is a side view of a preferred cannula embodiment for use with the trocar embodiment of FIGS. 12;

FIG. 13B is an end view of the cannula of FIG. 13A;

FIG. 14A is a side view of the trocar of FIGS. 12 received within the cannula of FIGS. 13;

FIG. 14B is an end view of the structure of FIG. 14A;

FIG. 15A is a side view of another preferred trocar embodiment;

FIG. 15B is an end view of the trocar of FIG. 15A;

FIG. 15C is a side view of another preferred cannula embodiment for use with the trocar embodiment of FIGS. 15;

FIG. 15D is an end view of the cannula of FIG. 16A;

FIG. 16 is a side view of another preferred trocar/cannula embodiment;

FIG. 17 is an isometric view of another preferred localizer embodiment with a rotatable bore array;

FIG. 18 is a view along the plane 18—18 of FIG. 17;

FIG. 21 is a view along the plane 21—21 of FIG. 17 illustrating a selectable bore array in place of the rotatable bore array of FIG. 17;

FIG. 22 is a side view of the structure of FIG. 21;

FIG. 23A is a side elevation view of the selectable bore array of FIG. 21;

FIG. 23B is a front elevation view of the selectable bore array of FIG. 23A;

FIG. 25A is a view similar to FIG. 24 illustrating a slidable bore array and compression plate;

FIG. 25B is a side view of the structure of FIG. 25A;

FIG. 26A is an isometric view of another preferred localizer embodiment having a slidable floor member;

FIG. 26B is a view along the plane 26B—26B of FIG. 26A;

FIG. 27A is a top plan view of a localizer having a conformable bore array;

FIG. 27B is a bottom elevation view of the localizer of FIG. 27A;

FIG. 27C is a side elevation view of the localizer of FIG. 27A;

FIG. 28 is a view of the localizer of FIGS. 27 installed on a patient for imaging and localization;

FIG. 29A is a side elevation view of a preferred localizer embodiment incorporating structure of the embodiment of FIGS. 27;

FIG. 29B is a top plan view of the localizer of FIG. 29A;

FIG. 32A is a side view of a drill-biopsy needle embodiment;

FIG. 32B is an end view of the drill-biopsy needle of FIG. 32A;

FIG. 33A is an enlarged view of structure within the curved line 33 of FIG. 32A illustrating a sampling end embodiment;

FIG. 33B is an enlarged view similar to FIG. 33A illustrating another sampling end embodiment;

FIG. 33C is an enlarged view similar to FIG. 33A illustrating another sampling end embodiment;

FIG. 33D is an enlarged view similar to FIG. 33A illustrating another sampling end embodiment;

FIG. 33E is an enlarged view similar to FIG. 33A illustrating another sampling end embodiment;

FIG. 33F is an enlarged view similar to FIG. 33A illustrating another sampling end embodiment;

FIG. 33G is an enlarged view similar to FIG. 33A illustrating another sampling end embodiment;

FIG. 33H is an enlarged view similar to FIG. 33A illustrating another sampling end embodiment;

FIG. 34A is an enlarged view of structure within the curved line 34 of FIG. 32A illustrating a driven end embodiment;

FIG. 34B is an enlarged view similar to FIG. 33A illustrating another driven end embodiment;

FIG. 35 is a side view of a vacuum syringe embodiment for use with the drill-biopsy needles of FIGS. 32–34;

FIG. 38 is a view along the plane 38—38 of FIG.37;

FIG. 39 is a top plan view of FIG. 38;

FIG. 40 is a computer monitor view showing a lesion scanning plane;

FIG. 41 is a computer monitor view showing a marker scanning plane;

FIG. 42 is an elevation view of an instrument embodiment for use in the system of FIG. 37; and FIG. 43 is a view along the plane 43—43 of FIG. 42.

DESCRIPTION OF PREFERRED EMBODIMENTS

Embodiments of the present invention may be directed to a plurality of specific imaging modalities, e.g., MRI, nuclear medicine and X-ray mammography. For clarity of description, the following preferred embodiments will generally be described with reference to the imaging modality of MRI after which their application to other modalities will be disclosed.

Figure 2:
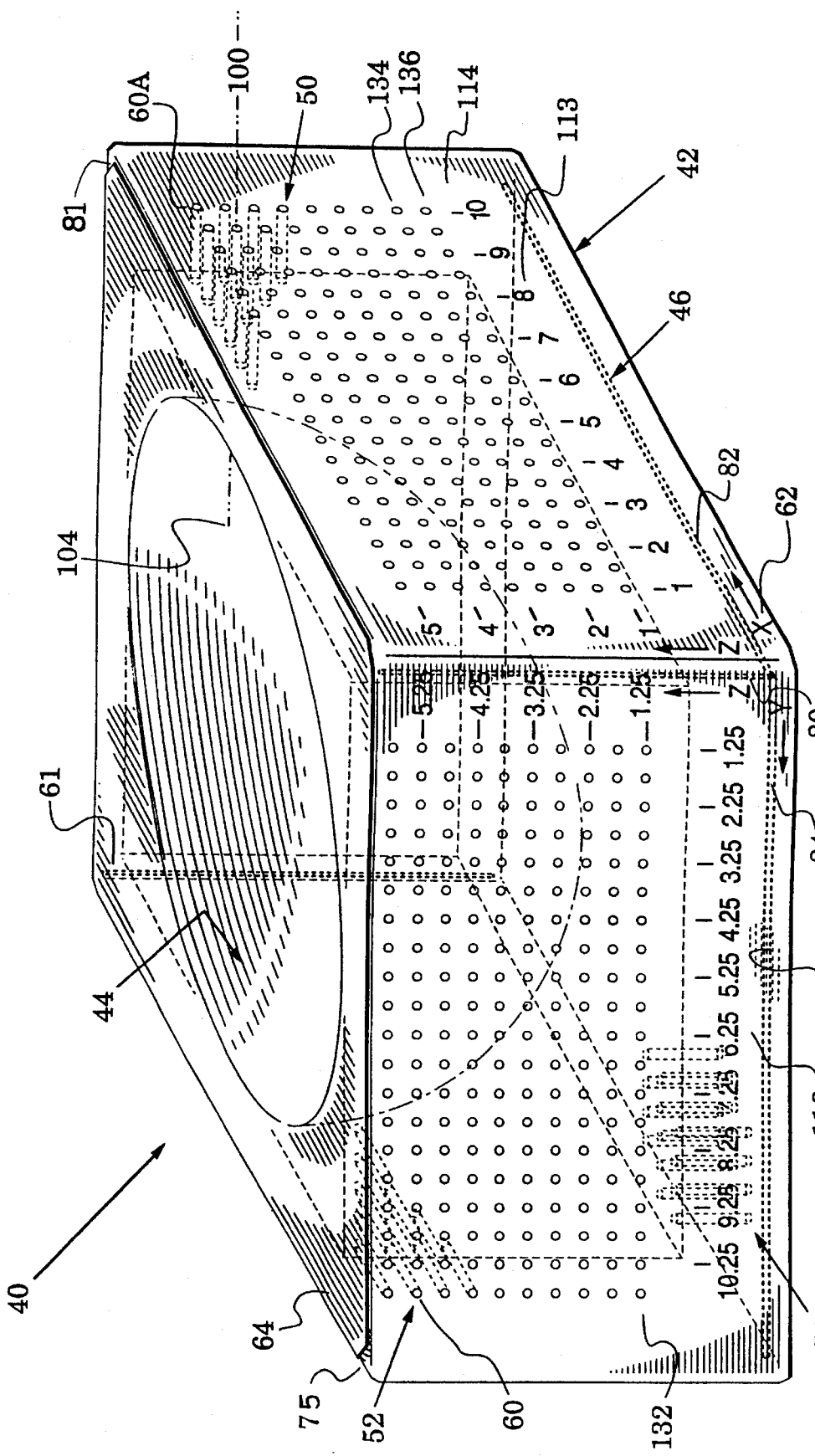
FIG. 2 is an isometric view of a preferred localizer embodiment, in accordance with the present invention.

FIG. 2 is an isometric view of a preferred localizer embodiment 40, in accordance with the present invent/on, having a frame 42 and a cup 44 carried by the frame. FIGS. 3A and 4A are respectively isometric and bottom plan views of the frame 42 and FIG. 5A is an isometric view of the cup 44.

As shown in these views, the frame 42 includes an MR signal-producing Cartesian coordinate system 46 and bore arrays 50, 52 and 54 aligned therewith (the array 54 is only partially shown in FIGS. 2, 3A for clarity of illustration). Each of the bore arrays includes a plurality of bores 60 defined by the frame 42. As an operational aid in its use, the localizer includes an MR signal-producing reference axis 61 and coordinate axes identifying indicia 62 in the form of x, y, z markers.

As specifically shown in FIG. 5A, the cup 44 has an inner surface 63 which is shaped and configured to closely receive a breast therein. In addition, the cup 44 defines a flange 64 extending from the cup rim 66 and a plurality of apertures 68 in the cup wall 69. For clarity of illustration, a limited number of apertures are shown but the apertures 68 may extend over the entire cup wall 69. The cup 44 is preferably formed of a thin nonferromagnetic, MR transparent material (i.e., one that is nonmetallic and does not produce an MR signal nor an MR artifact as defined in the background section) which is configured and positioned to stabilize the breast therein but which permits free transgression of a needle tip at any point by utilization of a high speed drill for needle insertion, e.g., rigid or pliable materials such as vinyl or plastic. Sterile fabric, paper, foam or a variety of conceivable materials may also be used by those skilled in the art. In accordance with a feature of the invention, a plurality of cups 44 are provided, each having a different volume defined between the inner surface 63 and the plane of the cup rim 66.

In use of the cups 44, the volume of a breast 70 to be MR imaged within the localizer 40 would be measured by insertion up to the chest wall 71 in a liquid 72 as shown in the schematic view of FIG. 6. The liquid 73 displaced from the container 74 is an accurate measure of volume of the breast 70. A cup 44 would then be selected from the plurality of cups in accordance with the measured breast volume.

The fit between the breast and the selected cup is further enhanced by the contour of the inner surface 63 which is generally breast shaped to define a confirming surface. For example, the inner surface may be formed in accordance with molds of actual breasts or formed to define a parabolic shape.

To further reduce movement of the breast surface relative to the cup wall 69, a surgical grade adhesive 75, e.g., dimethylpolysiloxane, may be applied to both through the apertures 68. For example, the adhesive could be applied by an applicator 76 as illustrated in FIG. 5A. Other effective application methods may be used, e.g., spraying through a thin tube or coating the interior of the cup. The use of suction through an aperture near the cup's inferior surface further enhances a close fit. A variety of methods to support the base of the cup relative to the localizer frame can be envisioned including a pillar 77 situated or attached between the inferior surface of the cup 44 and the localizer base as shown in the reduced view of FIG. 5B. FIG. 5B also shows the above mentioned suction applied by means of a syringe 78. The adhesive can be removed later with medical grade solvents, e.g., trichlorotrifluoroethane.

The breast and cup 44 are then arranged to have the cup 44 carried by the frame 42 as shown in FIG. 2 with, preferably, the medical grade adhesive 75 also applied between the flange 64 and a lip 76 defined by the frame 42 and between the flange 64 and the chest wall surrounding the breast. The localizer 40 and patient are then situated appropriately within an MR unit for imaging of the breast. Typically in this process, the patient lies in a prone position within the MR unit.

MR breast imaging would then be conducted as briefly described above in the background section and as well known to those skilled in the art. This imaging typically includes a fat suppressed 3D contrast-enhanced pulse sequence followed by maximum-intensity-projection (MIP) and rotational reconstruction of lesion coordinates. If the patient has a breast lesion, the imaged lesion 79 would appear on the MR computer display along with the MR visible coordinate system 46 of FIG. 2 which serves to define points in an imaging space within the coordinate system. This is illustrated in FIGS. 7A and 7B.

FIG. 7A represents a zero degree MIP projection of the contrast enhanced lesion 79 within the MR visible coordinate system (46 of FIG. 2) as viewed from above; the x and y coordinate axes 82, 84 are displayed en-face while the reference rod 61 and z coordinate axis 80 appear as points confirming exact zero degree rotation of the MIP projection. The x and y lesion coordinates 88, 86 are determined by measurement of perpendiculars to the y and x axes respectively.

FIG. 7B represents a 90 degree rotation of the MIP projection of FIG. 7A towards the right, corresponding to a left-lateral view of the coordinate system (46 of FIG. 2). This projection displays the x and z coordinate axes 82, 80 and the reference rod 61 en-face; the y axis rod 84 appears as a point confirming exact 90 degree rotation. The z lesion coordinate 90 is determined by measurement of a perpendicular to the x axis. For unambiguous identification of coordinate axes, an MR visible marker may be placed proximate to either the x or y axes. The reference rod 61, in conjunction with the z axis rod 80, defines the position of the lesion on individual coronal images of the contrast-enhanced fat-suppression MR study, and aids the MR technologist in positioning of slices.

With the x, y, z coordinates 88, 86, 90 determined, the nearest corresponding bore 60 can be chosen from any of the bore arrays 50, 52, 54. For example, if bore 60A in the bore array 50 meets this criteria, a medical instrument, schematically indicated by broken line 100, would then be guided (preferentially with the aid of a drill) through bore 60A until its tip 104 reaches the point represented by the coordinates 88, 86, 90.

Thus, within the resolution limits of the bore spacings of the array 50, the instrument tip 104 has been guided to the lesion site. The localization described above is preferably completed directly after imaging and without movement of the patient and localizer 40. The lesion 79, therefore, has not been moved relative to the coordinate system 46 during imaging and subsequent guidance of the medical instrument tip 104 to the lesion site.

The cup wall 69 is preferably formed as thin as possible to allow easy instrument penetration to minimize disturbance (i.e., maximize stabilization) of the breast subsequent to establishing lesion spacings. If desired, application of adhesive between the breast and cup wall 69 described above may effectively be restricted to those wall apertures 68 surrounding the bore selected in accordance with the imaged lesion spacings.

Suitable materials to form the cup 44 include plastic, vinyl, paper, particulate matter, foam, mesh and fabric or a variety of other materials conceivable by those skilled in the art. The apertures 68 may be omitted. Portions of the cup wall 69 may be omitted to lessen the tendency of the cup material to fold or wrinkle as it follows the breast contour and so that the breast may be seen if non-transparent cup materials are used. For example, quadrants could be removed from the wall 69 so that the remaining material forms an X shaped pattern. Means to secure the cup material to permit secure placement of the breast include straps placed around the torso of the patient, fasteners of numerous conceivable configurations on the localizer itself, or adhesive.

Returning attention now to details of the frame 42 as shown in FIGS. 3A and 4, the orthogonal Cartesian coordinate axes 80, 82 and 84 (which may be considered to be respectively z, x and y axes) are lumens (with the same reference number) defined by the frame 42 and filled with an MR visible material 85, e.g., Gd-DPTA liquid or other MR signal-producing material (which may be semisolid). The material in the lumens should be one that will produce an MR signal in all anticipated pulse sequences of the MR imaging. For example, mineral oil may produce an MR signal in many pulse sequences but, as opposed to Gd-DPTA, will not produce an MR signal in fat suppression sequences such as RODEO. The reference lumen 61 is diametrically opposed to (relative to the cup 44) and parallel with the lumen 80 to define another coordinate axis as an aid in identifying the cup area on the MR computer display.

In the embodiment 40, the frame 42 is formed of a nonferromagnetic, MR transparent material and defines a recess 112 to receive the cup 44. The bore arrays 50, 52 and 54 are arranged orthogonally and aligned in operative association with the coordinate axes 80, 82 and 84, i.e., arranged to be directed at an imaging space represented by the coordinate axes. Each bore axis defines a selected path that traverses the imaging space. The diameter of the bores 60 is selected to closely receive the instrument therethrough without excessive binding. Bore diameter and bore length are chosen to minimize deviation of the instrument tip 104 from the selected path of the bore axis as the instrument passes through the bore (it should be apparent that in all embodiment figures, only a few bores of each array have been shown completely for clarity of illustration).

For example, the bores of the array 52 in FIG. 4A have a space 141 between their axes. Each of these bores can guide the tip 104 of a medical instrument 100 (schematically indicated by the broken line 100) to an imaged location within the imaging space defined by the coordinate system 46. In FIG. 4A, the tip 104 is positioned substantially at the far side of this imaging space relative to the bore array 52, i.e., proximate to the wall 138. Ideally, the bores of the array 52 would be configured in diameter and length to guide the tip 104 without any deviation from the bore axis as it traverses the imaging space.

However, to enhance movement of the medical instrument in the bore, some variance between the dimensions of the instrument and the bore is desirable. FIG. 4B is a view of the structure within the curved line 4B—4B of FIG. 4A and FIG. 4C is a similar view. In FIG. 4B, the above mentioned variance is seen to allow an instrument 100 (e.g., a cannula) to rotate relative to the bore axis 142 until the instrument abuts bore edges 143, 144. In FIG. 4C, the instrument 100 has been rotated in the opposite direction until the instrument abuts the diametrically opposite bore edges 145, 146. Obviously, this rotation results in deviation of the instrument tip 104 from the bore axis 142. Reducing the bore diameter and/or lengthening the bore will limit this rotation and, hence, lessen the deviation of the instrument tip 100 from the bore axis 142. Thus, the bore diameter can be reduced and/or the bore length extended sufficiently to guide the instrument tip 100 within any selected maximum deviation from the bore axis as it traverses the imaging space. For example, if the selected maximum deviation were one half of the interbore spacing 141, the bore diameter would be reduced and/or the bore lengthened accordingly.

As an aid in selection of an appropriate bore 60 to select in guiding the instrument 100 in accordance with the MR computer display of FIGS. 7, array indicia 113 are provided on the frame faces 114, 116 and 118. These indicia indicate spacings of array rows and columns from the coordinate axes 80, 82 and 84 compatible with the spacing units used by the computer display.

Although the frame 42 is shown in FIGS. 2–4 to be integral, it preferably has removable lumens so that in cleaning of the localizer, the MR signal-producing material in the lumens is not subjected to excessive temperatures or other cleaning conditions that might degrade its performance. Accordingly, the frame may include removable lumens as shown, for example, in the partial sectional view of FIG. 3B where the frame is relieved along the frame faces 114, 118 and parallel to the lumen 82 to slidingly receive a conformingly shaped strip 119 which defines the lumen 82.

To increase the resolution capability of available guide bores, the spacing between the bores 60 in each array is selected to be as narrow as is practicable with the material and fabrication technique available. In accordance with a feature of the invention, after this spacing has been narrowed as far as is practicable, the arrays 50, 52 and 54 are arranged to be spatially interleaved, e.g., to each have elements such as rows and columns spatially interleaved with elements of other arrays. For example, as seen in FIG. 4A, row 120 of the array 54 is interleaved between columns 122 and 124 of the array 50 and column 126 is interleaved between columns 128 and 130 of the array 52. Similarly, row 132 of array 52 is interleaved with rows 134, 136 of the array 50 as shown in FIG. 2.

The imaging displays shown in FIGS. 7 may provide lesion spacings from all pairs of coordinates, i.e., from pair 80, 82, pair 80, 84 and pair 82, 84. An appropriate set of these spacings that most closely guides the instrument tip 104 to the lesion site can be selected. The array interleaving described above presents a greater resolution to this selection than would be otherwise be available.

With many medical instruments, e.g., a biopsy needle, the instrument can be withdrawn from the breast through the selected bore 60. However, some instruments can not, e.g., a hook-wire. Accordingly, FIG. 4A illustrates an embodiment variation in which the frame walls 137, 138 that respectively oppose the faces 114, 116 are separate and removable from the remainder of the frame. Thus after localization, the breast and attached hook-wire may be moved away from the faces 114, 116 so that the free end of the hook-wire can be withdrawn from its enclosing bore. The walls 137, 138 may be attached to the remainder of the frame 42 with conventional fasteners, e.g., screws 139, or with any well known quick-disconnect fastener of suitable nonferromagnetic and MR transparent material.

Figure 8:
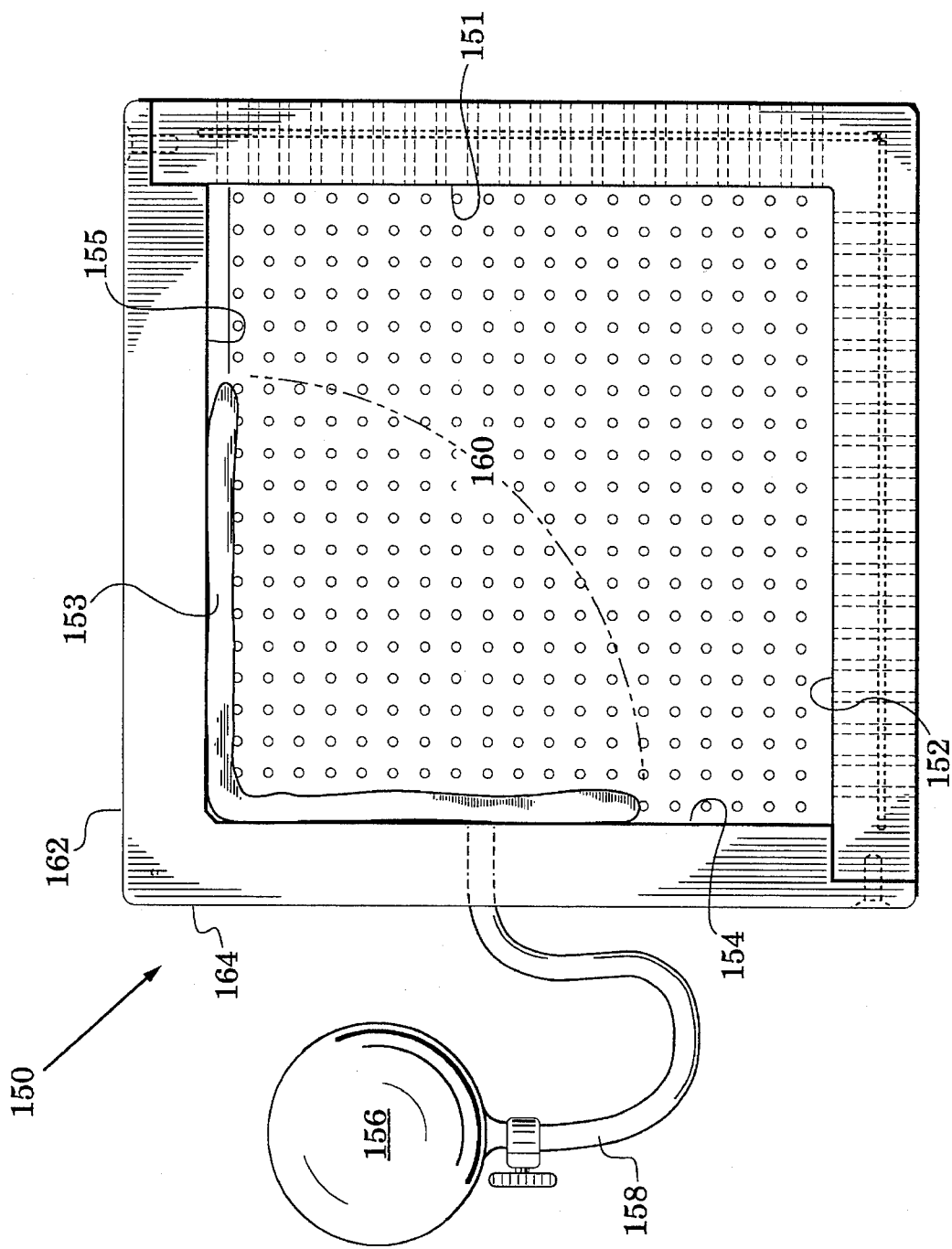
FIG. 8 is a top plan view of the localizer of FIG. 2 including removable walls and an inflatable bladder.

The top plan view of FIG. 8 illustrates another preferred localizer embodiment 150. The localizer 150 is similar to the localizer 40 of FIG. 2 but replaces the selected cup 44 with a combination of the interior frame faces 151, 152 and an inflatable bladder 153 disposed adjacent the respectively opposite interior faces 154, 155. By use of a resilient ball 156 and connecting tube 158, an operator can expand the bladder 153 as shown by the phantom line 160 to enclose and support the breast between the bladder 153 and the interior faces 154, 155. Of course, all materials of the bladder and associated structure preferably are nonferromagnetic and MR transparent. The embodiment 150 shows removable walls 162, 164 similar to the removable walls of FIG. 4A.

Figure 9:
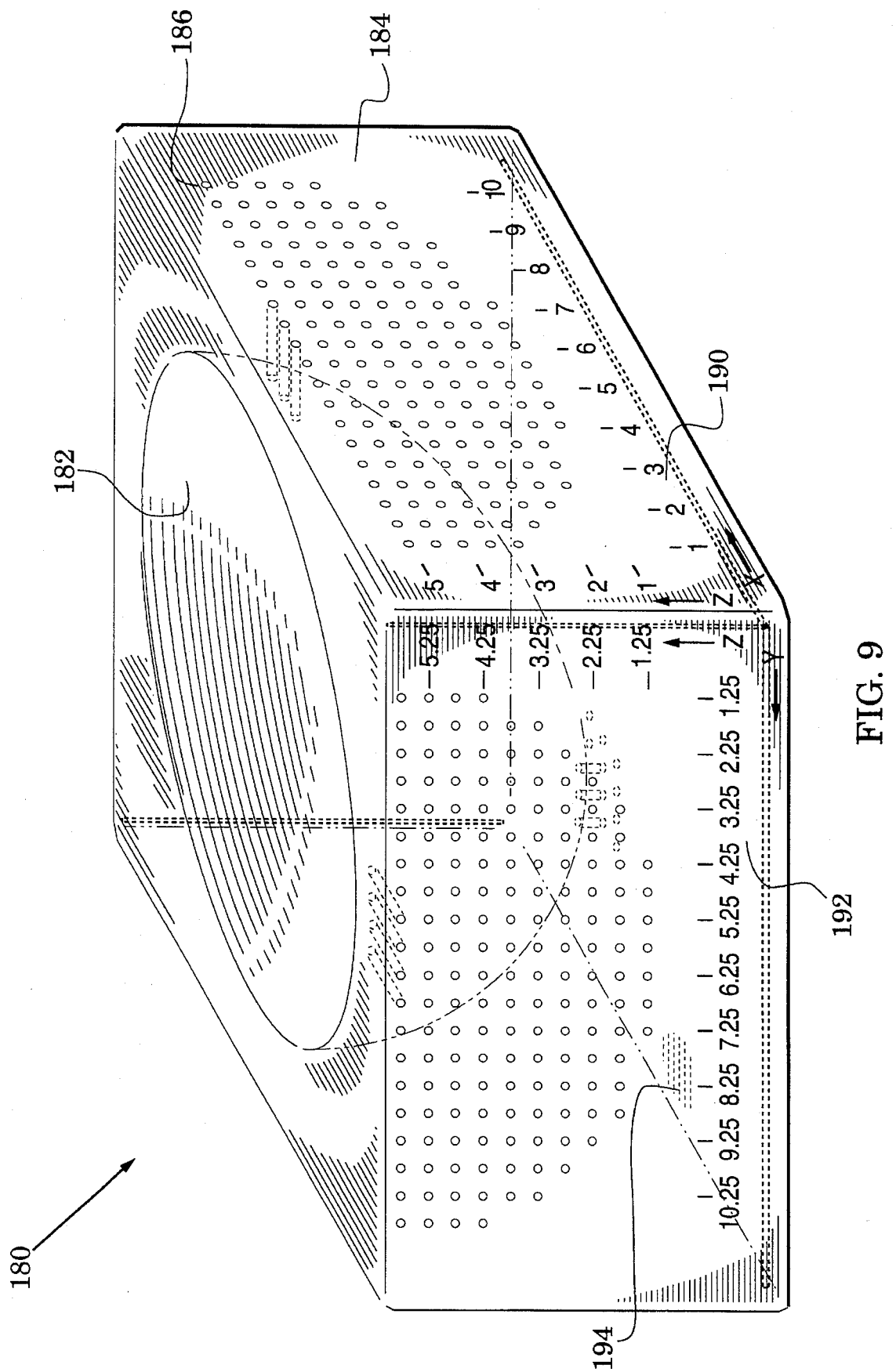
FIG. 9 is an isometric view of another preferred localizer embodiment.

Another preferred localizer embodiment 180 is illustrated in the isometric view of FIG. 9. The localizer 180 is similar to the localizer 40 but replaces the selected cup 44 with an interior breast receiving surface 182 defined by the frame 184. Thus all bores 186 are from the faces 190, 192 and 194 to the interior surface 182. The embodiment 180 permits the use of a simple frame to perform localization.

Figure 10:
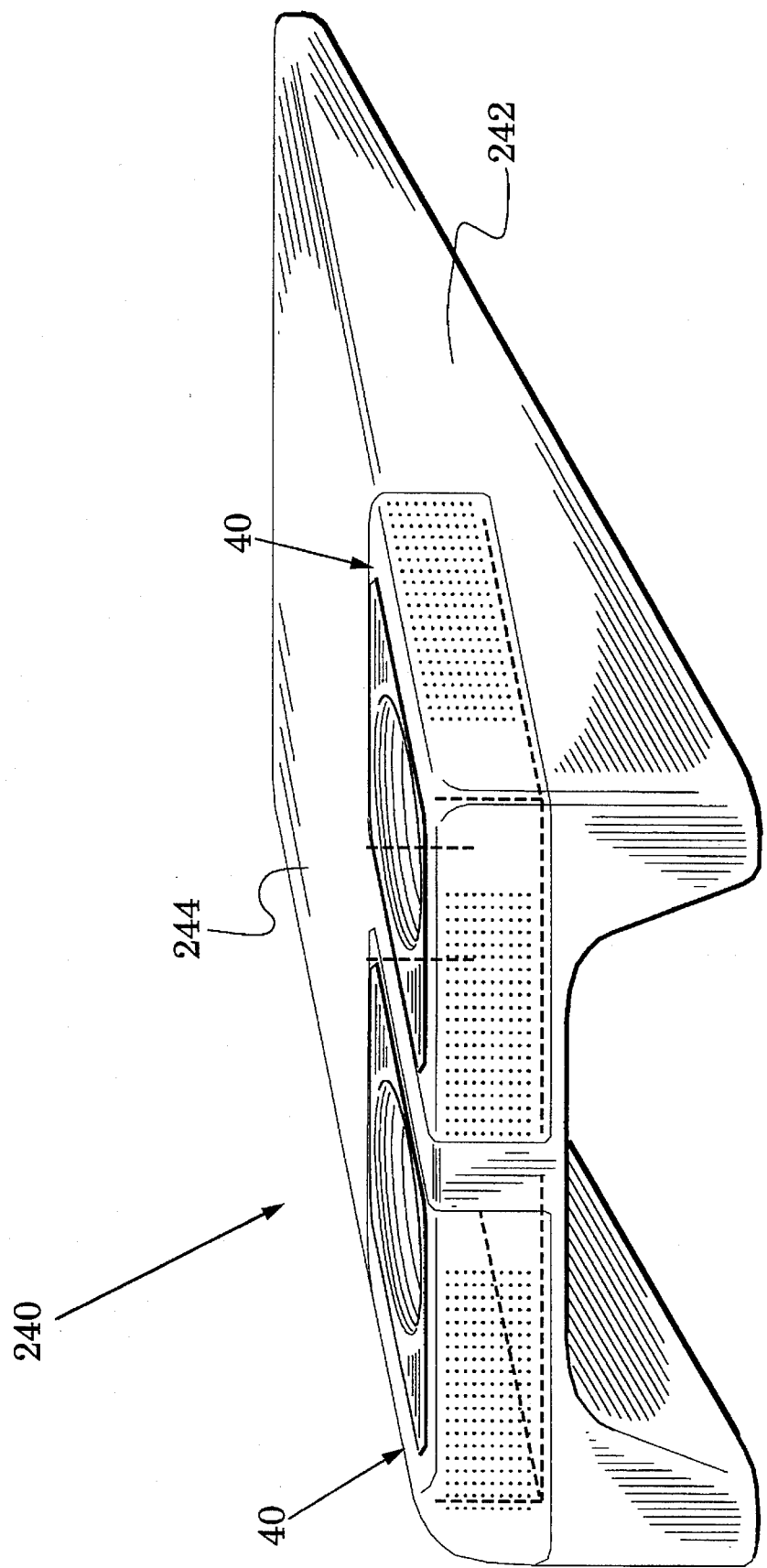
FIG. 10 is an isometric view of another preferred localizer embodiment.

The teachings of the invention can be extended to another preferred localizer embodiment 240 illustrated in FIG. 10. The embodiment 240 includes a housing 242 configured to present an inclined surface 244 against which a patient may comfortably be supported in a prone position within the MR unit. The housing 242 is configured to receive a pair of spaced localizers 40 (as shown in FIG. 2) so as to present them along the plane of the inclined surface 244. In use, the patient's breasts are received in the localizers 40 as described above. Imaging and guidance of medical instruments is then conducted as described above relative to other embodiments.

Figure 11:
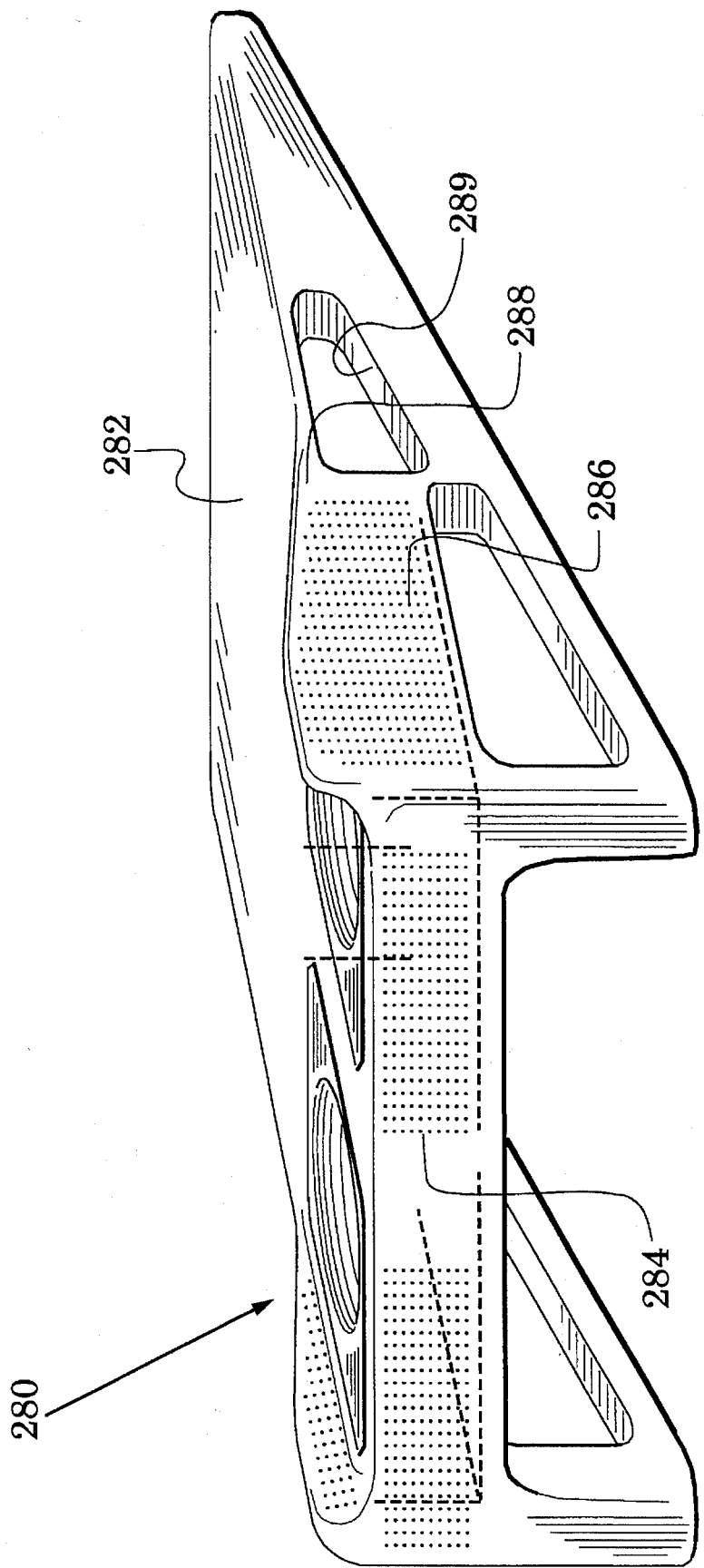
FIG. 11 is an isometric view of another preferred localizer embodiment.

Another preferred localizer embodiment 280 is shown in FIG. 11. The embodiment 280 is similar to the embodiment 240 but its housing 282 incorporates the localizers 40 of the embodiment 240 into a single unit, i.e., the localizers are not removable. The cranial and lateral grid faces 284, 286 may be slidingly removed, however, to permit sterilization. Additionally, the lateral edges 288 of the housing 282 and thus, the height of the lateral grid faces 286, may be increased as shown so that lesions closer to the chest wall may be approached laterally. The housing 282 also indicates exemplary reliefs 289 that may be designed thereinto by those skilled in the imaging art to accommodate breast imaging coils.

As mentioned above, it is desirable to minimize movement of either the breast or its supporting structure, e.g., the cup 44 of FIG. 2, during imaging and localization. In particular, such movement is preferably minimized during insertion of medical instruments for guidance to lesion sites. Accordingly, a preferred trocar/cannula embodiment 300, for use with the localizers disclosed herein, is shown in FIGS. 14A, 14B to have a trocar 302 and a cannula 320. In particular, the trocar 302 is shown in the side and end views respectively of FIGS. 12A, 12B. The trocar 302 has a cylindrical stem 304 that enlarges proximate a driven end 306 to an enlarged portion 307 which defines a stop 308 and, within the stop, a notch 310. This driven end and notch may be made of materials that include metal and plastic. The end 312 of the trocar terminates in a tip 332 which is preferably coaxial with the stem 304. It may be shaped with axially symmetric facets to minimize cutting forces that would force the trocar away from a penetration axis such as the axis of the bores of the localizer. For example, the embodiment 302 defines three cutting facets 314.

The embodiment 300 also includes a cannula 320 shown in the side and end views respectively of FIGS. 13A, 13B to have a passage 322 dimensioned to closely receive the trocar 302 for rotation therein. On a driven end 324, the cannula defines a tab 326 which is dimensioned to be received in the notch 310 of the trocar 302. On a leading end 328, the cannula defines an annular bevel 330 to minimize penetration resistance. Both trocar and cannula are formed from a nonferromagnetic and non artifact-producing material, e.g., titanium or stainless steel with a high nickel content, to be substantially MR transparent.

When the trocar 302 is received in the cannula 320 to form the embodiment 300 of FIGS. 14A, 14B, the enlarged portion 307 and cannula driven end 324 can be received together in the chuck of a driving apparatus, e.g., an MR-compatible compressed air drill. Engagement between the tab 326 and notch 310 further insures rotation of the trocar and cannula as one unit. The trocar/cannula 300 is suitable for guidance through localizer bores (60 in FIG. 2) to breast lesion sites because its axially symmetric facets, preferably rotated at high speed, e.g., 20–30,000 rpm, to enhance penetration, will minimize axial movement of surrounding tissue and structure, e.g., the cup 44, as it passes therethrough and minimize forces that would urge it from the bore axis as compared, for example, to a beveled needle that tends to be urged away from its bevel face as it passes through tissue.

The trocar/cannula 300 outer diameter is selected to be closely and rotatably received within the localizer bores (60 in FIG. 2). Indicia marks 338 may be added along the cannula to serve as indications of insertion depth within the localizer bores. These marks may also include numbers to indicate, for example, millimeter distances from the tip 332. To decrease penetration resistance, it may be preferable to create cutting edges by scooping the trocar facets 314. The enlarged portion 307 and cannula driven end 324 may define other shapes well known in the art for maximizing torque transfer thereto from the drill chuck, e.g., it could define a square cross section.

Once the tip 332 of the trocar has been positioned proximate to the lesion site, the trocar can be removed and the cannula 320 is suitably positioned for insertion of other instruments, e.g., a biopsy needle, a hook-wire or a laser fiber. In accordance with a feature of the trocar/cannula 300, the passage 322 of the positioned cannula is then substantially free of obstructing tissue.

Although a locking mechanism is optional, various equivalent structures can be used to lock the trocar and cannula together for penetration and yet allow subsequent withdrawal of the cannula. For example, in FIGS. 15A, 15B another trocar embodiment 350 has a constant diameter and defines a tab 352 which is dimensioned to be received in a notch 354 defined in the driven end 356 of the cannula 360 of FIGS. 15C, 15D. The tab and notch structures can be equivalently interchanged between cannulas and trocars.

FIG. 16 illustrates another trocar/cannula embodiment 370 having a cannula 372 with an enlarged head 374. The trocar 376 has a similar enlarged head 377 which abuts the head 374 when the trocar is fully received into the cannula 372. The heads 374, 377 may be formed of the same material as the shafts or of plastic secured therein. The plastic heads facilitate connection as a single unit and enhance securement in a drill chuck. The cannula and trocar may be locked together by a male or female thread 380 in the head 374 which receives a male or female thread 382 which may be located on the metal shaft 384 itself or on a sleeve extending forward from the head 377 which encloses the trocar shaft 384. Alternatively, the sleeve may be locked on the head 374, with female threads located within the head 377.

Other equivalent locking arrangements between the trocar and cannula may be devised by those skilled in the art. For example, the annular faces 386, 387 may define surfaces that rotationally grip each other. Exemplary surfaces would include ones that are undulating, zigzag and roughened. Still other embodiments include trocar/cannula systems without a locking mechanism defined therein but in which the trocar and cannula are both rotationally gripped by the drill chuck.

The teachings of the invention may be extended to rotatable, linearly movable, selectable alignment and conformable bore arrays. For example, FIG. 17 illustrates a preferred localizer embodiment 400 in which the upper row of the bore array 40 1 has been replaced by a rotatable array 402. The bore array 402 (consisting, in this embodiment, of a single row) is defined in a rotatable frame member in the form of a pivot bar 404 and the frame 406 is relieved along contour 410 to receive the pivot bar 404 therein. This relief permits use of the pivot bar without interfering with the cup 44 shown in FIG. 2. The pivot bar 404 particularly facilitates insertion of a medical instrument to lesions that are deeper than the chest wall which is typically abutted by the frame lip 412 during imaging and localization (it should be understood from the disclosure above that the imaging space defined by the frame's coordinate system extends past the frame lip 412).

FIG. 18 is an enlarged view along the plane 18—18 of FIG. 17. FIGS. 17 and 18 show a medical instrument, schematically indicated by the broken line 414, inserted through a bore 416 to where the instrument tip 420 has been guided to the coordinates of a lesion site determined during breast imaging with the embodiment 400. FIG. 18 also indicates a pivot pin 422 for mounting of the pivot bar 404 to the frame wall 424.

In use of the embodiment 400, the x lesion coordinate determined during imaging would be used in selecting the bore of the pivot rod 404 for insertion of the medical instrument 414. The y, z coordinates would be transformed by standard trigonometric relations to polar coordinates r, theta. With these coordinates, the pivot bar 404 is then set at the angle theta (reference number 432 in FIG. 18) and the medical instrument inserted through the selected bore by a distance r.

In particular, assuming the pivot pin 422 is in the same plane as the lumens 80, 82 of FIG. 17, the transformation to polar coordinates is performed by obtaining a dimension z' which is the imaged coordinate z less the vertical distance from the lumen 82 to the pivot pin 422. The coordinates y, z' are then referred to the pivot pin 422 and r and theta, relative to the pivot pin, given by standard transformations of theta=arctan z'/y and r=y/cos theta.

In accordance with the teachings above, other rotatable array embodiments may be formed in which the pivot bar 404 and frame 406 are modified to convert any row or partial row or any column or partial column of the arrays 401, 428 and 430 to a rotatable array.

Figure 19:
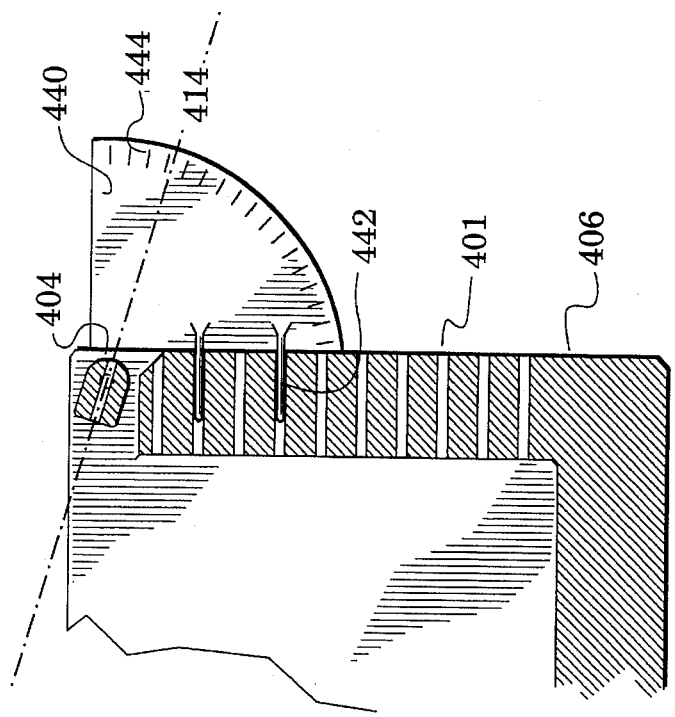
FIG. 19 is a view along the plane 19—19 of FIG. 17 illustrating a polar coordinate guide.

FIG. 19 is a view along the plane 19—19 of FIG. 17 illustrating a protractor 440 that includes pins 442 which can be inserted into a selected column of the bore array 401 shown in FIG. 17. Rotational indicia 444 on the protractor 440 facilitate alignment of the pivot bar 404 and an inserted medical instrument 414 in accordance with the derived lesion angle theta.

Figure 20:
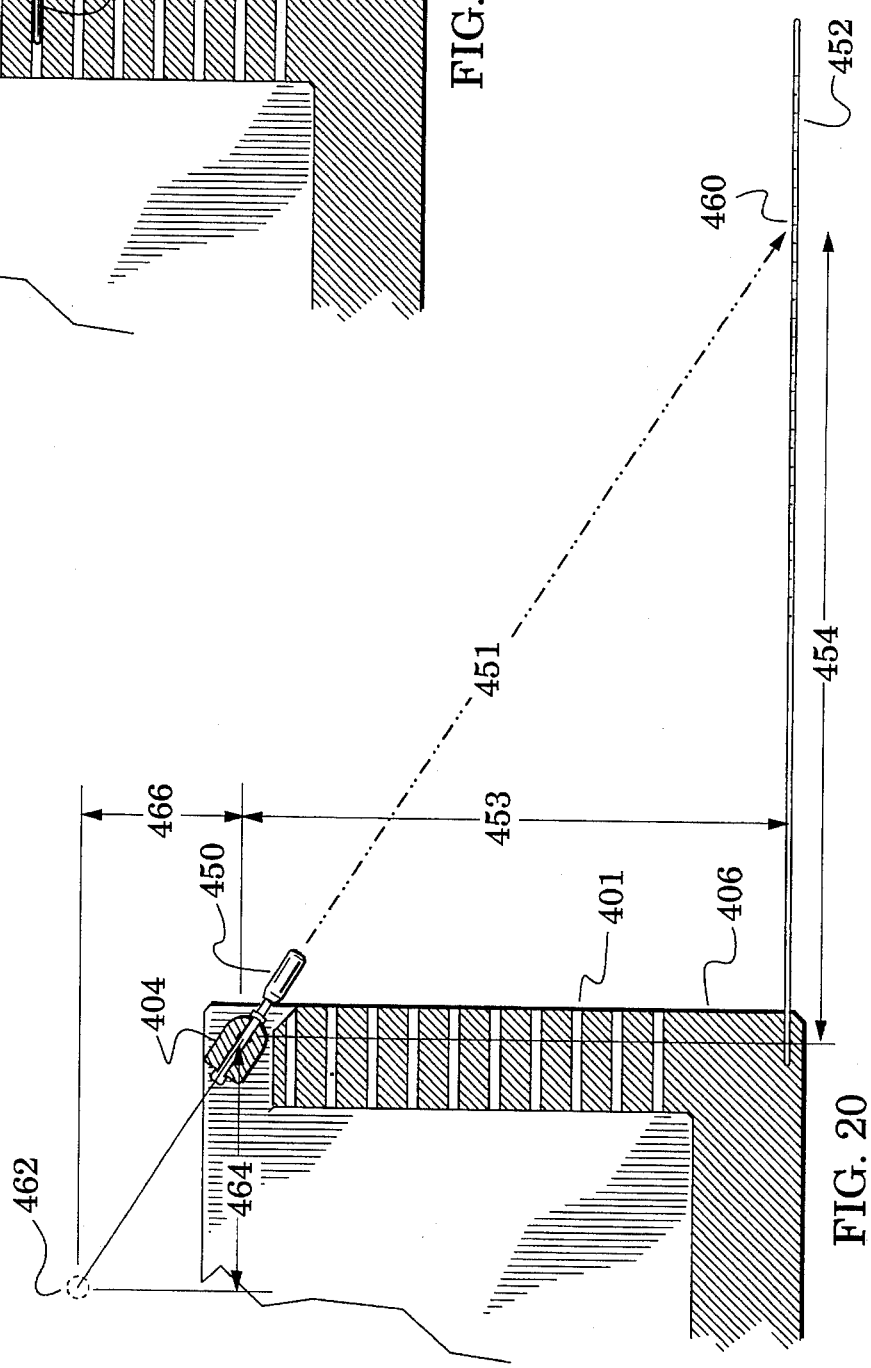
FIG. 20 is a view similar to FIG. 19 illustrating another polar coordinate guide.

FIG. 20 is a view similar to FIG. 19 showing a laser 450 installed in a bore of the pivot bar 404 so that it directs a laser beam 451 onto a reference rod 452 extending from the frame 406. Knowledge of y, z and the structural distance 453 are sufficient to determine distance 454 along the reference rod so that there is no need to directly to calculate the angle theta. Thus, the pivot bar 404 may simply be rotated until the laser beam 451 strikes an indicia 460 at the distance 454 along the reference rod 452. In particular, the imaged coordinates y, z to a lesion 462 are respectively distance 464 and distance 453+466 and, by the theory of similar triangles, 466/453=464/454 so that the distance to be indicated on the reference rod is 454=464(453/466) or 454=453(y/z').

The laser beam 451 may be directed to the pivot bar 404 from a remotely located laser via an optical fiber. For example, a laser source is often associated with MR units so that a laser beam could be provided therefrom rather than from a separate laser source as shown in FIG. 20. Therefore, a structure equivalent to that shown in FIG. 20 could be an optical fiber routed from a remote laser to have its termination mounted in the pivot bar 404 in place of the laser 450. It should also be understood that various equivalent distance indicating structures may be substituted for the reference rod 452, e.g., a plate or sheet extending from the frame 406 or even any structure separate from the frame having indication of known distance therefrom.

Selectable alignment bore arrays may also be effectively used to reach chest wall lesion locations. FIG. 21 is a view along the plane 21—21 of FIG. 17 illustrating the pivot bar 404 replaced by a frame member in the form of a selectable array block 480 while FIG. 22 is a side elevation view of the structure of FIG. 21. FIGS. 23A and 23B are respectively side and front views of the array block 480.

In these views, the array block is shown to define an array consisting of a single row 484 of bores at an angle 486 to the mounting surface 488. This angle is the angle theta derived above from the imaging coordinates y, z'. The array block defines a pair of tenons 490, extending downward from the mounting surface 488, which are slidingly received in a matching pair of mortises 492 cut in the frame 494 to end short of the frame face 496. The array block 480 is thus automatically positioned when it is inserted to where the tenons 490 abut the end of the mortises 492.

In practice, a series of array blocks 480 would be provided, each having bores directed along a different spatial angle theta, e.g., in steps of one degree. In use, a given array block would then be selected in accordance with the derived angle theta. Mortises would then be selected to receive the array block so that one of the bores of the array 484 is positioned as close as the bore resolution permits to the x coordinate found during imaging. A medical instrument 414 can then be inserted through the selected bore by a distance r (or a compensated distance calculated from the face 498 of the array member). Various structures functionally equivalent to the mortises 492 and tenons 490 may be easily devised by those skilled in the art to facilitate insertion of array blocks into the frame.

In accordance with the above disclosure, other selectable alignment bore array embodiments may be formed that convert any row or partial row or any column or partial column of the arrays 401, 428 and 430 (see FIG. 17) to a selectable alignment array.

Figure 24:
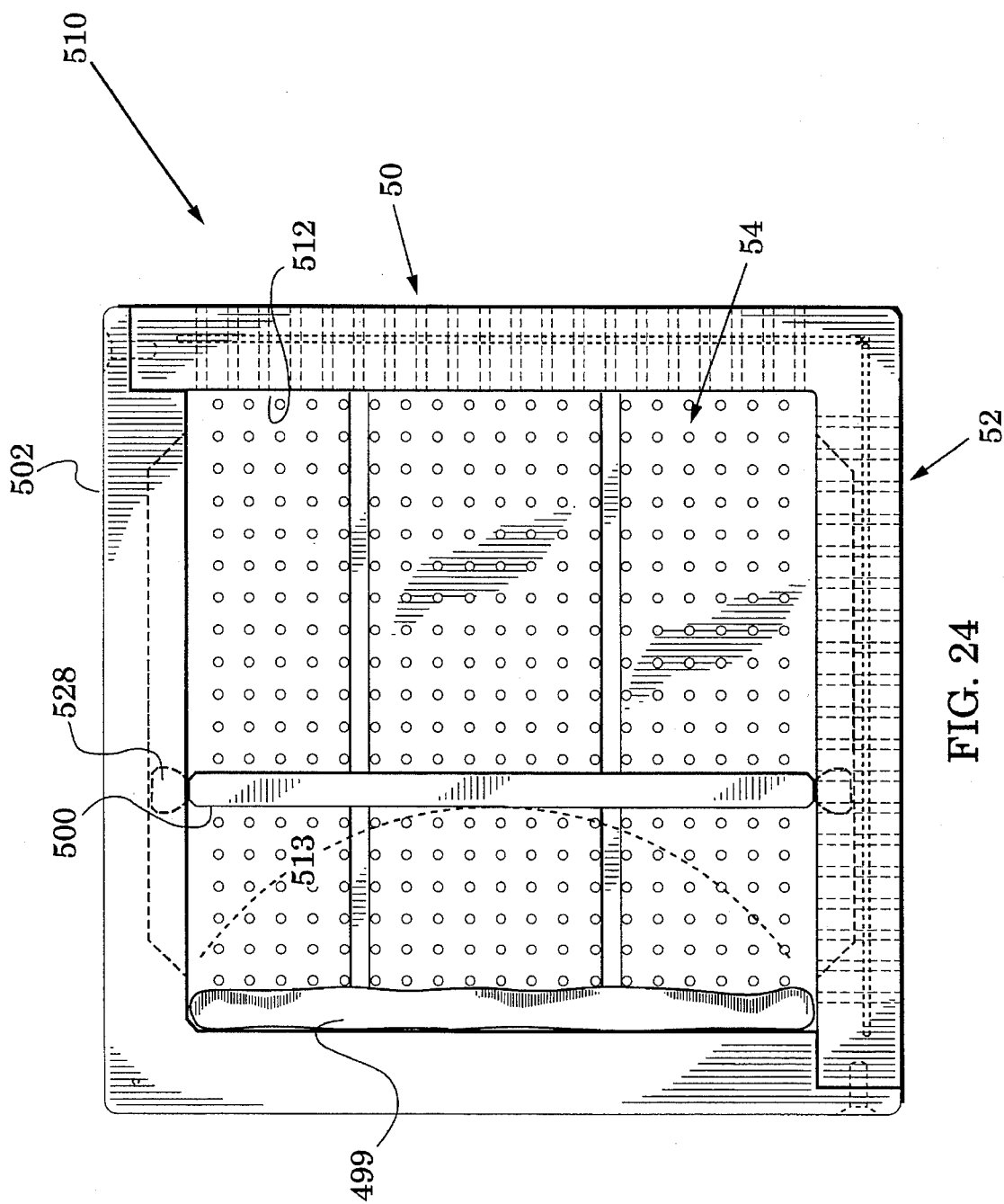
FIG. 24 is a view similar to FIG. 8 illustrating a slidable compression plate.

Preferred embodiments of the invention include linearly movable frame walls and bore arrays as shown in FIGS. 24, 25A and 25B. FIG. 24 is a view similar to FIG. 8 in which an inflatable bladder 499 (similar to the bladder 153 of FIG. 8) is combined with a plate 500 sliding within the bore frame 502. In this localizer 510, a breast may be stabilized for imaging and localization by minimal compression between the plate 500 and the frame face 512 when the bladder 499 is expanded as indicated by the broken line 513. These embodiments may be used without entrapment of the breast since, if adhesive is not used, the breast may be freely removed without causing pain to the patient. The degree of breast compression is minimal and serves only to eliminate free space within the frame recess and to locate the grid face proximate to the skin surface.

Similar functions are provided by the localizer 520 shown in top plan and side elevation views respectively of FIGS. 25A and 25B. The localizer 520 includes a slidable plate 522 and a slidable frame member 524 within a U shaped frame 526 in which the frame member defines a bore array 525. Movement of the plate 522 and frame member 524 may be stabilized by vanes 528 extending therefrom to be slidably received in slots 530 and 532 cut respectively in frame inner faces 534, 536 and floor 538. Alternatively, the elements 528 may be rollers which are rotatably received in arcuate grooves 530, 532. Similar movement structure may be provided for the plate 500 of FIG. 24. Movement of plates may be accomplished by inflatable inserts or mechanically by a number of methods known to those skilled in the art.

In use, the patient's breast would be minimally compressed between the slidable bore array 525 and the plate 522 (or between the plate 500 and frame face 512 of the localizer 510) after which imaging and localization would proceed as disclosed above. The positions of the bore array 525 and plate 522 relative to the frame 526 may be locked by any conventional means, e.g., thumb screws, latches.

Another preferred localizer embodiment 560 that includes apparatus directed to breast stabilization is illustrated in FIG. 26A. The localizer 560 is similar to the localizer frame 42 of FIG. 3 but carries a compression plate 562 within the recess 564. An inflatable bladder 566 is disposed between the compression plate 562 and the floor 568. Inflation of the bladder 566 can cause the compression plate 562 to move vertically as indicated by the double headed arrow 570 to vary the spaced relationship between the plate 562 and the floor 568. A variety of mechanisms may be used to cause vertical movement of the compression plate.

In use, the patient's chest wall would abut the upper lip or face 572 allowing the breast to depend within the recess 564. The bladder 566 is then inflated to push the compression plate 562 upward to support and stabilize the breast. Preferably, an MRI volume imaging coil is disposed about the localizer 560. Alternatively, a surface coil may be adjacent the lower face 574 of the compression plate 562. Thus, the surface coil would remain adjacent the breast as the compression plate 562 rises.

The x, y coordinate system lumens 576, 578 may be snapped into selected ones of a plurality of vertically spaced grooves. Thus, the lumens may be placed adjacent the upper face 579 of the compression plate 562. This is illustrated in FIG. 26B which is a view along the plane 26B—26B of FIG. 26A. The x coordinate lumen 576 is received into a selected one of the vertically spaced grooves 580 defined in the face 581. If desired, the grooves 580 can be undercut to further enhance retention of the lumens. Alternatively, the lumen 576 (and lumen 578) may be carried in the movable compression plate 562 as shown in FIG. 26B.

To insure that the compression plate 562 remains substantially horizontal as it rises within the recess 564, it may be closely fitted to the walls of the recess 564 and have sufficient vertical thickness to be guided and restrained by the recess walls to be orthogonal thereto. Nonmetallic ball or roller bearings 582 may be carried in the sides of the compression plate 562 to reduce friction between the plate and the recess walls. The bladder 566 may carry stiffening plates 584, 585 on each side thereof. These plates ensure that the upper surface of the bladder defines a plane to thereby exert a uniform pressure along the lower face 574. In the embodiment 560, a medical instrument can be guided to an imaged lesion through bores 586 in bore arrays 588, 589 while movement of the breast is limited by the compression plate 562 and the inner walls of the recess 564.

The preferred embodiments illustrated in FIGS. 24, 25 and 26 are especially suited for use where breast compression techniques are considered necessary. Other movable wall and array embodiments may be formed in equivalent ways to convert any bore array (e.g., bore arrays 50, 52 and 54 of FIG. 3A) to a linearly movable array.

Preferred embodiments of the invention include localizers having bore arrays conformed to body portions associated with the breast. Such an embodiment is shown in FIGS. 27 and shown installed over a body portion in FIG. 28 The localizer 600, illustrated in plan, bottom elevation and side elevation views respectively of FIGS. 27A, 27B and 27C, has an MR visible coordinate system formed by lumens 602, 604 and 606. These lumens are filled with an MR visible material to create an imaging coordinate system functionally similar to that of the lumens 80, 82 and 84 of the frame 42 of FIG. 3A. The lumens are defined within a frame member 608 which also defines a bore array 610 arranged in operative association with the coordinate system.

In the localizer 600, however, the lower face 612 of the frame member 608 is shaped to conform to the axilla and the adjacent pectoralis muscle. Specifically, a face portion 614 is shaped and spaced from the frame upper face 616 to conform to the axilla and a face portion 618 is shaped and spaced more narrowly from the face 616 to conform to the pectoralis muscle. The lower face 612 descends along one side of the frame member 608 to form a side plate 619 that contains the lumen 606.

In use, the localizer 600 would be placed on a patient 620 as shown in FIG. 28. The lower face 612 abuts the patient with the face portion 614 received in the axilla hollow and the side plate 619 extending downward along the side of the patient 620. A medical adhesive may be placed between the patient and the lower face 612 to reduce movement therebetween. For additional stabilization, straps 622 may extend from the localizer to enclose the patient's body. A flat rf imaging coil may be located above the localizer.

The localizer 600 is particularly intended to image and localize nodes within the axilla for needle biopsy sampling and lesions within the "Tail of Spence" (axillary tail). Other embodiments may have bore arrays shaped to conform with other specific body regions, e.g., the neck, the abdomen.

Conformable structures and bore arrays therein similar to the localizer face 612 of FIGS. 27 may be combined with structures similar to the localizer 180 of FIG. 9 to form the localizer 640 illustrated in the side and top views respectively of FIGS. 29A, 29B. The frame 642 of the localizer 640 defines, in its upper surface, an arcuate, e.g., parabolic, breast receiving depression 644 similar to the surface 182 of FIG. 9. The frame 642 also defines an arm 646 extending cranially and laterally relative to the remainder of the frame body.

The floor 647 of the frame rises to define the floor 648 of the arm 646. The arm 646 defines an upper surface 650 shaped similar to the face 612 of FIGS. 27B, 27C, i.e., to conform with the axilla and the adjacent pectoralis muscle. For example, the surface 650 includes a downward extending trough 651 shaped to receive a pectoralis muscle and the overlying axillary tail (tail of Spence) therein. The trough 651 transitions laterally and caudally into an upward swelling mound 652 shaped to fill the axilla region. The surfaces 644, 651 and 652 smoothly transition into each other. The side wall 654 rises to an upper margin 657 that is higher than the remainder of the frame 642 (indicated by broken line 658). This upper margin 657 transitions smoothly laterally and cranially into the mound 652.

The side wall 654 defines a horizontally directed bore array 655 therein (the array is only partially shown in FIG. 29B for illustration clarity). The bores of this array open into the lateral side of the depression 644. The side wall 654 transitions at an angle into the side wall 656 of the arm 646. The arm 646 defines a vertically directed bore array 659 which opens into the anterior surfaces of the mound 652 and trough 651 (the array is only partially shown in FIG. 29B for illustration clarity).

Lumens 662 and 663 in the side wall 654 respectively define coordinate axes z and y while a lumen 664 extends orthogonally away from the side wall 654 to define an x axis coordinate. Another lumen 666 in the side wall 656 defines a y' coordinate axis while a lumen 668 extending orthogonal to the side wall 656 defines an x' coordinate axis. The lumens 666, 668 are contained above the raised arm floor 648.

In use, the localizer 640 would be arranged so that the arm 646 extends cranially and laterally relative to a patient. The patient's breast would be received into the depression 644 and the axillary tail (tail of Spence) and underlying pectoralis muscle received in the trough 651. The upward extending mound 652 would fill the axilla region. After imaging, medical instruments can be inserted to reach lesion sites through bores selected in accordance with the imaging. Lesion sites within the breast would generally be located relative to the lumens 662, 663 and 664 and reached through the bore array 655 while lesions in the tail of Spence would generally be located relative to the lumens 662, 666 and 668 and reached via the bore array 659. The upward extending side wall 654 facilitates the approach of lesion sites above the chest wall with the bore array 655.

In an alternative embodiment, the surfaces 644, 651 and 652 may also be defined in an insert that is formed of a thin nonferromagnetic, MR transparent material and the insert removably mounted within a frame in a manner similar to the cup 40 and frame 42 of the localizer 40 of FIG. 2. In applications where compression is deemed desirable, compression techniques described in other embodiments herein may be applied. For example, structure disclosed in FIGS. 26 may be incorporated with the localizer 640 of FIGS. 29. That is, a compression plate and bladder similar to the compression plate 562 and bladder 566 of FIGS. 26 may be used. The compression plate would be shaped to conform to the surfaces 644, 651 and 652.

Figure 30:
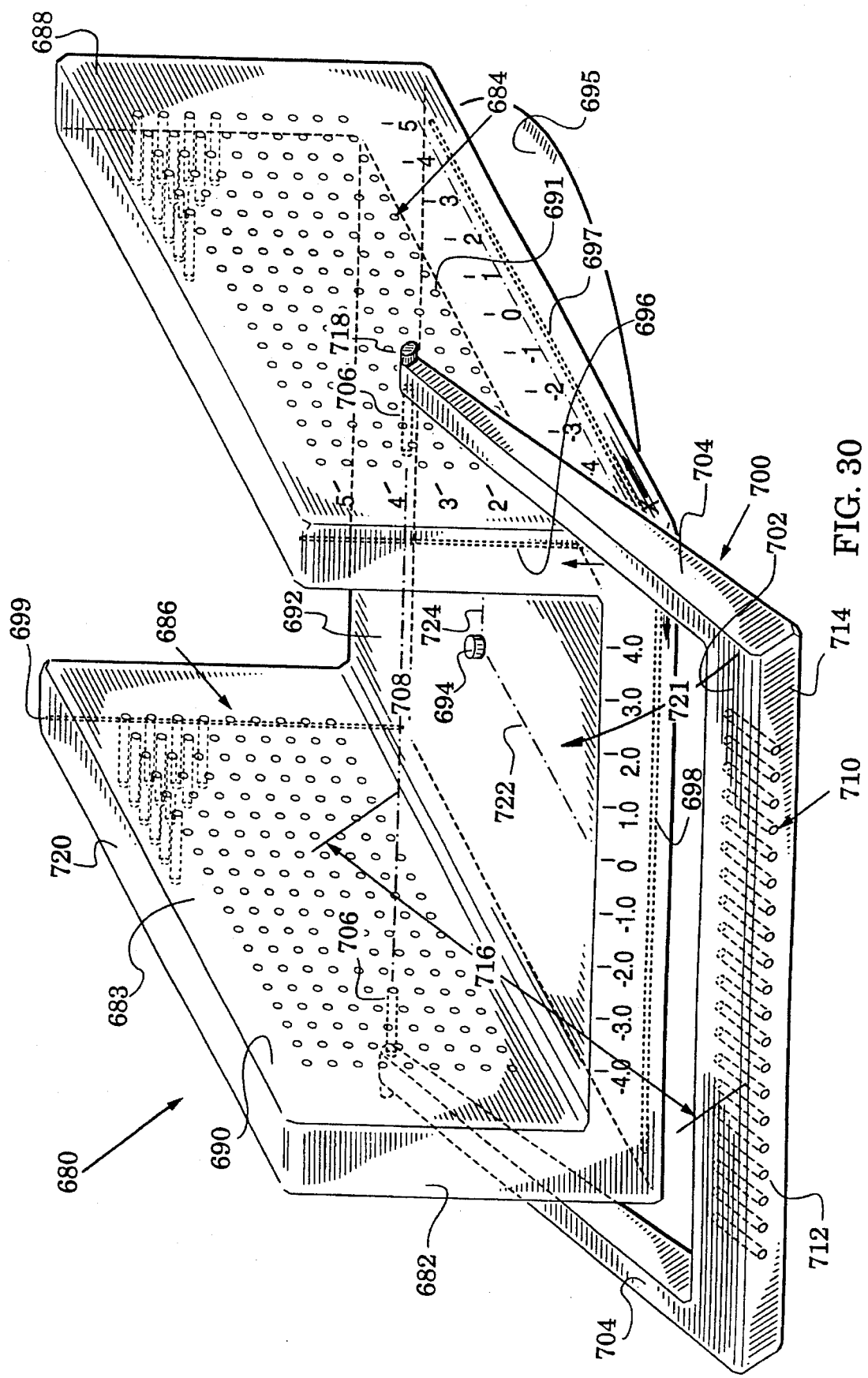
FIG. 30 is an isometric view of another preferred localizer embodiment illustrating a rotatable arm carrying a bore array.

Preferred localizer embodiments of the invention also include pivotable arms which carry bore arrays. These structures facilitate the selection of preferred paths for guidance of a medical instrument to an imaged lesion. For example, FIG. 30 is an isometric view of a localizer 680. The localizer 680 has a frame 682 similar to the frame 42 of FIG. 3A but with two opposing walls removed to leave a U-shaped frame that defines a recess 683 therebetween. Bore arrays 684, 686 are defined in the two remaining spaced and opposed walls 688, 690. Each bore 691 in one of these arrays is coaxial with a bore of the opposed bore array. The walls 688, 690 are connected by the orthogonally arranged floor 692 and a pin 694 pivotably attaches the floor 692 to a supporting housing. The supporting housing is not shown for clarity of illustration but could be one similar to the housing 242 of FIG. 10. Such a housing could also carry a protractor 695 for measuring the angular position of the frame 682. Orthogonal lumens (coordinate axes) 696, 697, 698 and 699 are defined by the frame 682 similar respectively to the lumens 80, 82, 84 and 61 of the frame 42 of FIG. 3A.

A U-shaped arm 700 includes a bar 702 carried between the outer ends of two legs 704. Each inner end of the legs 704 has a pin 706 and the pins 706 are each coaxial with an imaginary axis 708 therebetween. A transversely arranged bore array 710 is defined in the bar 702. Each bore 712 of the bore array 710 is directed radially away from the axis 708, i.e., a projection of the axis of any of the bores 712 intersects the axis 708, and the outer face 714 of the bar 702 is arranged a distance 716 from the axis 708. The pins 706 can be removably inserted into selected coaxial bores of the opposed bore arrays 684, 686. To facilitate this removable insertion, the pins 706 can, for example, be spring loaded in the legs 704 and moved axially in and out by means of a knob 718. Arm 700 may employ several rows of bores, each directed towards the pivot axis. Although the bores are preferably directed at the pivot axis 708, the arm 700 may carry bores with other alignments.

When using the localizer 680, and in particular the arm 700, a breast is positioned within the recess 683. The breast may be stabilized with the aid of structures disclosed above, e.g., a cup similar to the cup 40 of FIG. 2 could be carried from the lips 720. Bores would be selected in bore arrays 684, 686 in accordance with the imaging data relative to the 696, 697 coordinates (i.e., the opposed bores whose axis 708 most nearly intersects the imaged lesion are selected) and the pins 706 inserted therein. Next, a bore of the bore array 710 is selected in accordance with imaging data relative to the 698 coordinate (i.e., the bore nearest the y axis location of the lesion is selected).

A medical instrument is placed in the selected bore in the bore array 710 and inserted, from the face 714 a distance equal to the distance 716. This will place the tip of the medical instrument proximate to the center of the lesion. The arm 700 can be rotated about its mounting pins 706, as indicated by the arrow 721, to select a specific path from the selected bore to the lesion, e.g., a path that allows sampling of the lesion at a different angle by drill-needle biopsy. Because the pin axis 708 has been aligned with the lesion, the arm 700 can be placed at any angle and an insertion depth of distance 716 will still place the medical instrument tip proximate to the lesion.

Each of the opposed bores, selected in the bore arrays 684, 686 in accordance with the imaging data, can also be used directly for guidance of a medical instrument to the imaged lesion site. In this option, the instrument is inserted a depth selected in accordance with the imaging data relative to the 698 coordinate.

In either case, the frame 682 can also be pivoted about the pin 694 to select a specific path from any of the bore arrays 684, 686 or 710 to the imaged lesion. If the frame 682 is pivoted an angle φ between imaging and localization, the imaged lesion coordinates must be converted accordingly. To simplify this conversion, the zero indicia indications on the coordinate axes 697, 698 are aligned with the pivot pin 694 as indicated by broken lines 722, 724. The converted imaged data relative to the x, y coordinates (lumens 697, 698) is x'=x cos φ+y sin φ and y'=y cos φ−x sin φ. The imaged distance along the 696 axis, of course, remains unchanged.

The localizer 680 may also include an upward directed bore array in the floor 692 similar to the bore array 54 of FIG. 2. Additionally, other embodiments of the invention may have bore array carrying arms that are pivotably mounted in selected bores of this floor array rather than in the wall arrays as illustrated in FIG. 30.

Figure 31:
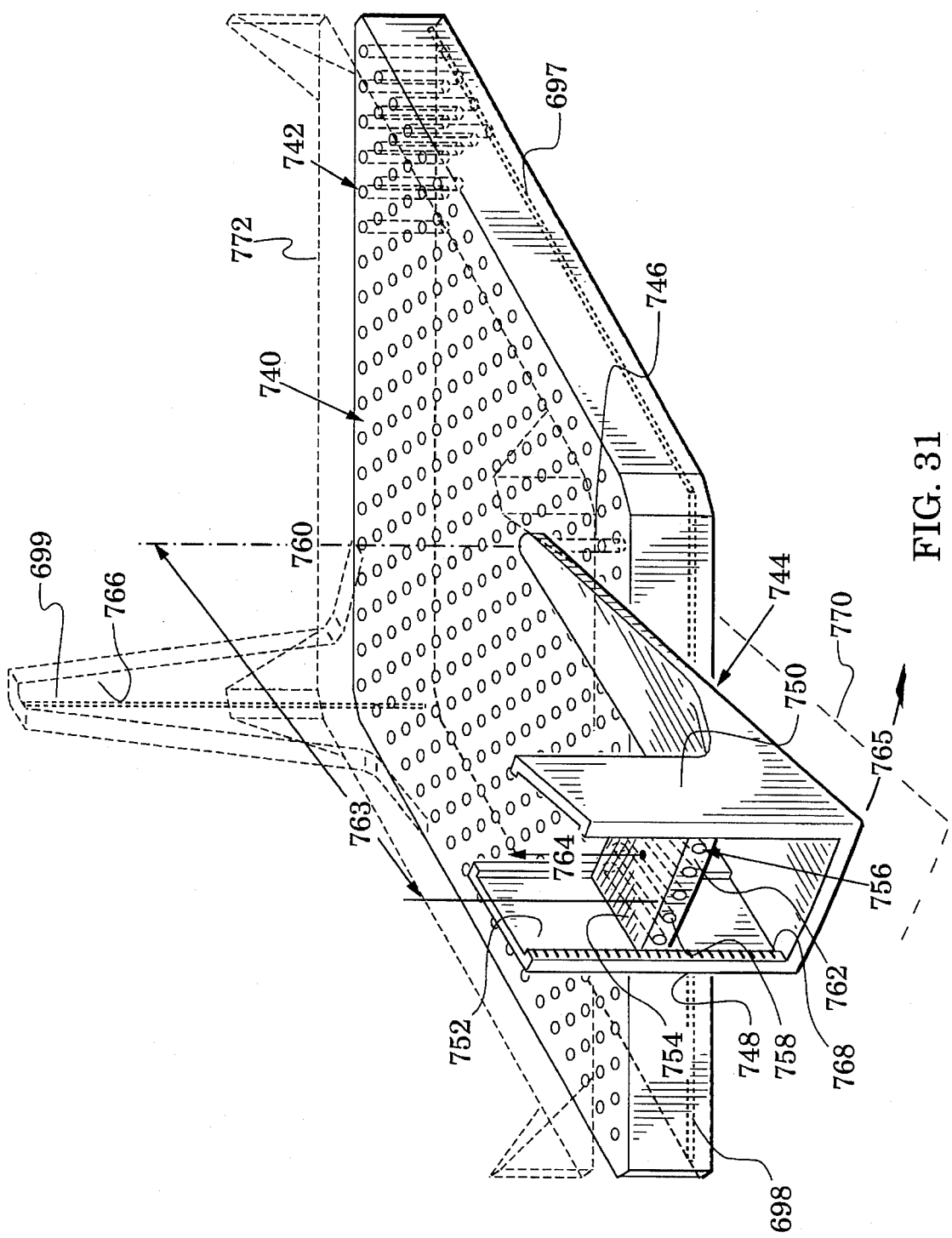
FIG. 31 is an isometric view of another preferred localizer embodiment illustrating a rotatable arm carrying a bore array.

For example, FIG. 31 shows a plate 740 similar to the floor 692 which defines a bore array 742. The plate 740 may be a separate plate or may represent the floor 692 of the localizer 680 of FIG. 30. An arm 744 has a downward extending pin 746 at its inner end and defines a pair of horizontally spaced upward extending guides 748, 750 at its outer end. Each of the guides 748, 750 defines a vertically oriented recessed track 752. Slidably mounted in the tracks 752 is an array block 754 which carries a bore array 756 oriented in a horizontal plane. Each bore 758 in the bore array 756 is directed inward and rotated horizontally so that its axis intersects the vertical axis 760 of the pin 746. The face 762 of the array block is curved so that any point in the face is a horizontal distance 763 from the pin axis 760. The array block 754 slides up and down in the tracks 752 as indicated by the arrow 764.

The plate carries lumens 697, 698 and 699 similar to the identically numbered lumens of FIG. 30. The upward extending lumen 699 would be in the localizer 680 if the plate 740 is the floor 692 thereof. Otherwise, the plate 740 may define an upward extending portion 766, shown in broken lines, to carry the lumen 699.

When using the plate (or floor) 740, a bore can be selected in bore array 742 in accordance with the lesion imaging data relative to the 697, 698 coordinates and the pin 746 inserted therein. Next, the array block 754 is adjusted to vertically align each bore 758 with the imaged lesion in accordance with imaging data relative to lumen 699. Indicia such as the marks 768 may be provided to aid this alignment. The array block 754 may carry bores either in parallel or which have long axes intersecting the pin axis 760. Although the bores are preferably directed at the pin axis 760, the array block 754 may carry bores with other alignments. Several rows of bores may also be employed.

A medical instrument may then be placed in any bore of the bore array 756 and inserted, from the face 762 a distance equal to the distance 763. This will place the tip of the medical instrument proximate to the center of the lesion. Different bores of the bore array 756 may be selected and/or arm 744 can be rotated about its mounting pin 746, as indicated by arrow 765, to select a specific path from the selected bore to the lesion, e.g., a path that intersects a different part of the lesion. Because the pin axis 760 has been vertically aligned with the lesion, the arm 744 can be placed at any angle and an insertion depth of distance 763 will still place the medical instrument tip proximate to the lesion. The inner end of the arm 744 is shown to lie above the plate 740. As indicated by broken lines 770, the arm 744 could also be mounted below the plate 740 with the pivot pin 746 directed upward into the bore array 756. This arrangement would avoid interference with the breast or breast supporting structures above the plate 740. When the arm 744 is disposed above the plate 740, a thin membrane 772 (shown in broken lines) may be carried above the plate 744 to space the breast from the arm 744.

Alternatively, the bore selected in the bore array 742 (or arrays 684, 686 in the localizer 680 of FIG. 30) in accordance with the imaging data can also be used directly for guidance of a medical instrument to the imaged lesion site. In this option, the instrument is inserted a depth selected in accordance with the imaging data relative to the 699 coordinate when using the array 742 and relative to the coordinate 698 when using the arrays 684, 686.

When the arm 744 and plate 740 form part of the localizer 680 of FIG. 30, i.e., the plate 740 represents the floor 692 of the localizer, the opposed open ends of the U-shaped frame 682 allow passage of medical instruments from the array block 754 to imaged lesion sites. Other equivalent localizer frames may be visualized to provide access between the array block 754 and imaged lesion sites, e.g., an L-shaped localizer frame including the floor 692 and one of the walls 688, 690 of the frame 682. It should be understood that because the arms 700, 744 can be installed subsequent to imaging, they do not necessarily have to be made of MR transparent material.

Trocar/cannula embodiments associated with the invention were disclosed above and illustrated in FIGS. 12–16. As stated above relative to those figures, after the tip of a trocar, e.g., trocar 350 of FIG. 15A, has been positioned proximate to the lesion site, the trocar can be removed and its associated cannula, e.g., cannula 360 of FIG. 16A, is suitably positioned for insertion of other instruments.

One example of an insertable medical instrument is an emulsifier (morcelator). Another example of an insertable instrument is the hollow drill-biopsy needle 780 illustrated in side and end views respectively of FIGS. 32A and 32B. The biopsy needle 780 is similar to the trocar embodiment 350 of FIGS. 15. Accordingly, the needle 780 defines a driven end 820 (having a tab 782) which is dimensioned to be received in the chuck of a high-speed drill. The driven end 820 may be augmented by metal or plastic (similar to the cannula/trocar 370 of FIG. 16) and may have various dimensions all of which permit optimal stabilization of the needle by the drill chuck. Thus, the needle 780 can be inserted into the cannula 360 with the needle sampling end 784 extending out of the cutting end of the cannula and into the imaged lesion. In practice, the length of the biopsy neeedle should be longer than that of the cannula/trocar.

Various structures may be defined in the sampling end 784 to retain lesion tissue as the biopsy needle 780 is withdrawn from the cannula. For example, FIGS. 33A–33H are enlarged views of the sampling end 784 (structure within the curved line 33 of FIG. 32A) that illustrate irregularities directed to retention of lesion tissue. FIG. 33A shows a beveled cutting edge 786 at the sampling end 784. FIG. 33B shows a toughened surface comprising random irregularities 788 defined in the interior of the sampling end 784. The irregularities may extend radially inward from the interior surface 790 to form tiny bumps or extend radially outward to form small pits. FIG. 33C shows random scroll lines 792. Similar to FIG. 33B, these lines may extend radially inward to form ridges or radially outward to form grooves in the interior surface 750. FIG. 33D illustrates a slanted hole 794 defined in the wall of the sampling end 744. FIG. 33E illustrates annular barbs 796 while FIG. 33F illustrates annular grooves 798. FIG. 33G shows focal, i.e., local in nature, steps 800 and barbs 802. FIG. 33H illustrates cutting tabs 804 extending axially from the sampling end 784 to form a trephine. The irregularities may be formed of either metal or plastic and may be coaxially inserted and fixed during needle manufacture. The needles themselves, as well as the trocar/cannula, may be made entirely of synthetic material such as reinforced plastic.

The biopsy needle 780 is driven by a high-speed drill to extend the sampling end 784 past the cannula (preferably positioned at the margin of the lesion) and into the lesion tissue. The sampling end 784 thus cuts a core sample of the lesion. Retention of this sample is enhanced by the irregularities. Since withdrawal of the needle may permit the core sample to slide out of the sampling end 784, aspiration (suction) is preferably employed to pull the sample into the needle shaft prior to needle removal from the breast.

A vacuum syringe 810 which facilitates retention of the core tissue retained in the sampling end 784 is shown in FIG. 35. The syringe 810 has a plunger 812 within a cylinder 814 which terminates in a reduced end 816. When the plunger 812 is withdrawn from the cylinder end 816, a partial vacuum is created inside the cylinder 814. A removable resilient diaphragm 818, e.g., rubber, is carried over the end 816. The driven end 820 of the biopsy needle is inserted through the diaphragm 818. Since the biopsy needle is longer the cannula, when the plunger 812 is withdrawn the drilled core tissue in the sampling end 784 will be sucked down and retained within the shaft of the needle towards the driven end 820. When the needle is subsequently removed, the entire drilled core sample will be within the shaft of the needle. FIGS. 34A, 34B are enlarged views of the structure within the curved line 34 of FIG. 32A. FIG. 34A illustrates the same driven end shape of FIG. 32A while FIG. 34B illustrates that the driven end terminates in a beveled tip 822 which facilitates penetration of the diaphragm 818.

Figure 36:
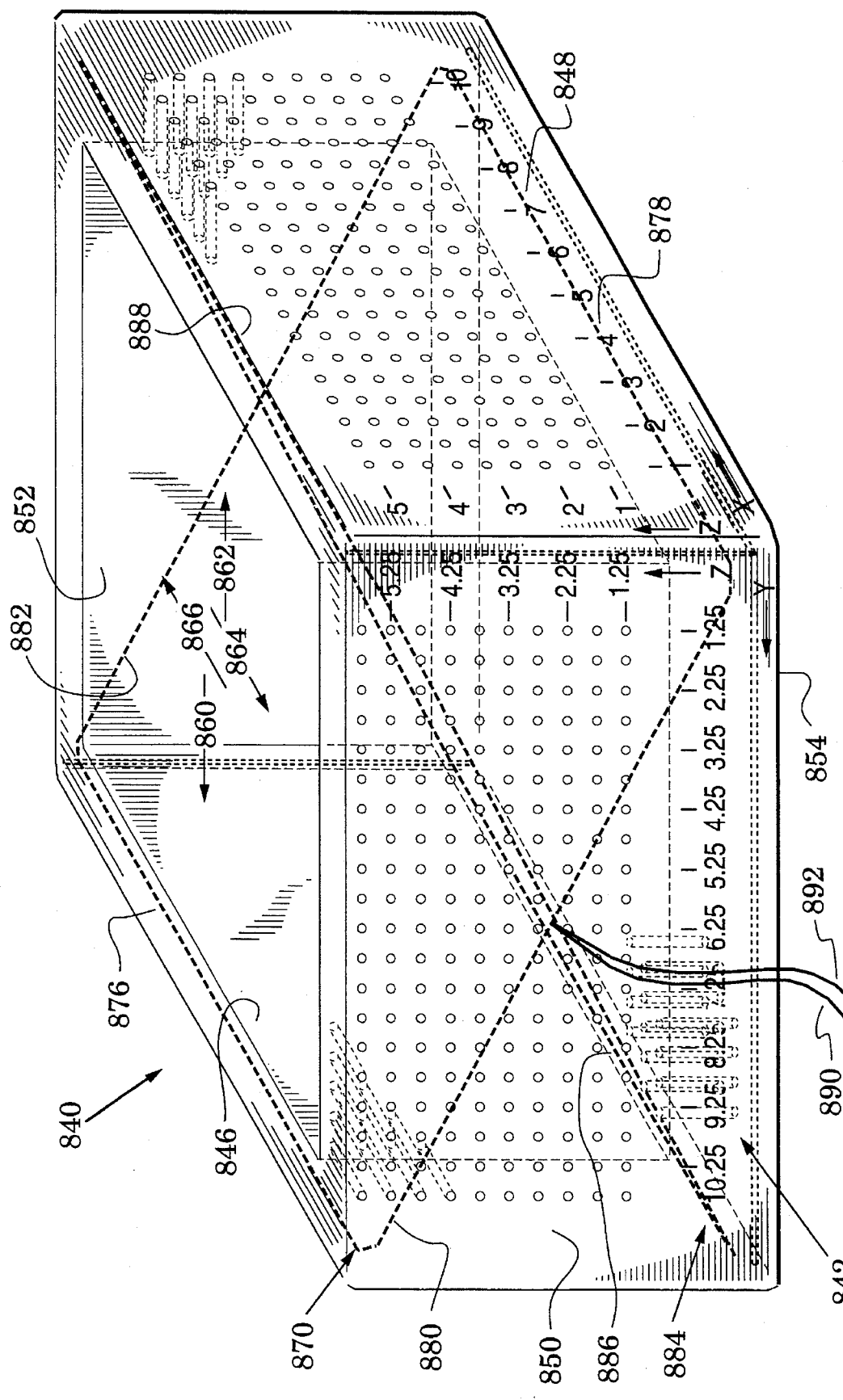
FIG. 36 is a view similar to FIG. 3A illustrating incorporation of MRI transmit/receive coils in the frame of FIG. 3A.

The localizer structures taught in the present invention may incorporate therein transmit/receive coils well known in the MRI imaging art for generating rf excitation signals and receiving the tissue emitted response signals. As briefly described in the background section, these coils typically include surface coils, whole-volume coils (in solenoid, saddle and birdcage configurations), partial-volume coils, intracavitary coils and coil arrays. For example, FIG. 36 illustrates a frame 840 similar to the frame coil 42 of FIG. 3A with transmit/receive quadrature coil set 842 contained therein.

The frame 840 has medial and lateral walls 846, 848 and cranial and caudal walls 850, 852 extending upwards from a floor 854. These directions are also indicated by the medially directed arrow 860, the laterally directed arrow 862, the cranially directed arrow 864 and the caudally directed arrow 866. The coil set 842 includes a single turn coil 870 of copper wire or band which has sides 876, 878 respectively disposed within walls 846, 848 and ends 880, 882 respectively disposed within walls 850, 852. One microfarad capacitors are typically located at several points along the coil to enhance RF signal characteristics. A similar coil 884 is disposed within the frame walls but rotated to have its sides 886, 888 vertically spaced from the sides of the turn 870.

Isolated leads 890, 892 provide independent connection to the coils (typically through a diode). In ways well known in the MRI imaging art, the coils 870, 884 carry currents in quadrature, i.e., 90 degrees out of phase and are controlled with quadrature circuit boards within or external to the frame 840. Although the coils 870, 884 are shown integrally molded into the frame 840, they may be carried by the frame in other equivalent ways, e.g., mounted with spacers to the external wall faces. The crossed coils 870, 884 are each shown in FIG. 36 to have a rectangular shape. In other embodiments, the coils may be of the crossed ellipse type in which each coil defines an elliptical shape.

In the interest of descriptive clarity, the preferred embodiments have been illustrated with reference to the specific imaging modality of magnetic resonance imaging. However, the inventive concept is generally directed to a variety of imaging modalities. For example, in the exemplary imaging modality of MRI, the coordinate systems are configured to carry an MR signal-producing material but they generally would be configured to be visible in the selected imaging modality.

A first example of another selected imaging modality is nuclear medicine in which emissions of radioactive substances are typically used to interrogate a patient's tissues. With this specific imaging modality, the coordinate systems of the invention are accordingly modified to carry a radioisotope that is visible to nuclear medicine detectors, e.g., a scintillation camera. Preferably, a dilute solution of the radioisotope injected in the patient would be used because the detectors would generally be compatible with that radioisotope. The breast would then be imaged using techniques well known in the nuclear medicine art (described, for example, in Introductory Physics of Nuclear Medicine, Chandra, R., Lea & Febiger, Philadelphia, 1987, the disclosure of which is hereby incorporated by reference).

A first exemplary use of the invention in nuclear medicine imaging would include placing a small rectangular parallel hole collimator and detector positioned parallel to the grid faces (e.g., the faces 114 and 116 of FIG. 2) sequentially or placing two such collimators and detectors on the x, z and y, z grid faces simultaneously. With a high resolution detector the x, y and z coordinates of a breast lesion, which uptakes a radioisotope, can be determined for localization and biopsy in accordance with the above disclosure. Radioisotopes currently known to be breast-cancer-avid include Tc99m Sestamibi and Thallium-201 (as reported, for example, by R. J. Campeau, et al., Concordant Uptake of Tc-99m Sestamibi and Tl-201 in Unsuspected Breast Tumor, Clinical Nuclear Medicine, 1992 (12): p 936, 937, the disclosure of which is hereby incorporated by reference). Detectors providing high spatial resolution such as solid-state designs may be employed.

In a second exemplary use of the invention in nuclear medicine imaging, SPECT (single photon emission computed tomography) would be used followed by three dimensional computer rendering to determine lesion coordinates in the same manner as described above for maximum-intensity-projection (MIP).

In a second example of another selected imaging modality, the teachings of the invention may be extended to X-ray mammography or CT scanning by configuring the coordinate system to be visible therein. For example, the coordinate system could include radio-opaque rods such as rods that carry an iodinated contrast material. When using a focal spot in this modality, corrections for parallax must be corrected to align the imaged lesion in reference with the central ray, e.g., using trigonometric calculations from a plurality of angled views.

In a third example of another selected imaging modality, ultrasound may be used to determine a lesion's coordinates from three grid faces defining x,z; y,z; and x,y planes. In this modality, the location of the ultrasound transducers comprises the visible coordinate system, i.e., distances to an imaged lesion are referenced to each transducer face which defines one of the above mentioned planes. Needle insertion may then proceed as described herein. The frame would be of a material transparent to the ultrasound. The transducers may be positioned, e.g., hand held, adjoining the frame array faces.

To appraise the viability of the inventive concepts, a prototype localizer was fabricated in accordance with preferred embodiment 150 of FIG. 8 but without the bladder 153. The frame was formed of lucite with 2 millimeter diameter mineral oil filled lumens (mineral oil was used because no fat suppression sequences were anticipated). The array bores were 0.040 inch in diameter, 4 millimeters long and spaced 5 millimeters apart. A phantom target cube of adipose tissue having 5 millimeter sides was held within a larger (11×11×6 cm) foam phantom disposed within the frame.

The prototype was imaged within the head coil of a 1.5 Tesla system (Signa; GE Medical Systems, Milwaukee, Wis.) and spacings from the coordinate system rounded to the nearest 5 millimeters. Using these coordinates, a 19.5 gauge core-biopsy gun (Argon Medical, Athens, Tex.) was guided through bores selected in accordance with the imaged spacings and to a depth in accordance with the imaged spacings. One bore was selected in each of two different arrays. In each case, the needle tip was placed within the target and the biopsy gun fired to yield a small core.

From the foregoing, it should now be recognized that localizer embodiments have been disclosed herein especially suited for guidance of medical instrument tips to a breast lesion site in accordance with lesion spacings derived with the aid of imaging visible coordinate systems. Additionally, trocar/cannula embodiments suitable for use with the localizer embodiments have been disclosed. Preferred embodiments also include bore arrays configured to be rotated, linearly moved, selected for alignment, conformed to patient body regions and carried on pivotable arms.

Embodiments of the invention directed to the use of substantially noncompressed breast techniques offer several potential advantages. As particularly shown in embodiment 40 of FIG. 2, the cup 44 is selected to closely receive and support the patient's breast during both imaging and instrument guidance. Thus, the breast is not subjected to discomfort resulting from pressure or distortion as in some present stabilization techniques which use more than minimal compress/on between plates. Possible rupture or other damage to a breast implant is also avoided.

Because the breast is supported while in the localizer, the breast tissue may be presented without compression to minimize interference with contrast dynamics and subsequent d/agnostic interpretation. Also, relative movement between the breast and inserted markers (e.g., hook-wires, carbon trails) upon removal from the localizer should be reduced compared to compression techniques.

Again, if the breast is not subjected to more than minimal compression, normal spacing between multiple lesions is maintained. This may allow improved spatial selectivity of lesion treatments. For example, laser fibers can be directed specifically to each of two spaced lesions whereas, under breast compression, the lesions may be so close together that healthy tissue is also subjected to laser energy. In addition, if forcible compression is used, lesions may be driven towards the skin surface increasing the risk of skin necrosis if these lesions are treated by percutaneous laser therapy. Such compression may also collapse vascular structures which inhibits contrast enhancement of lesions.

Where compression techniques are deemed necessary, other embodiments of the invention are provided which include linearly movable bore arrays, inflatable inserts or compression plates. These structures are directed to the support and stabilization of the breast during imaging and localization with minimal compression but without entrapment of the breast, i.e., the breast can be removed at any time from these structures without discomfort.

With embodiments of the invention, access to breast lesions may be obtained through each bore array. In addition to providing increased resolution of instrument placement and alternate routes to a lesion to avoid, for example, another proximate lesion, this feature also offers instrument guidance perpendicular to the chest wall, e.g., through bore array 54 of FIG. 2, which may be advantageous in reaching lesions near the chest wall.

Other embodiments in accordance with the invention include rotatable bore arrays, bore arrays with selectable bore angle alignments and bore arrays carried on pivotable arms. These embodiments are particularly suited for imaging and localization of lesions within the chest wall. Still other embodiments include frame members shaped to conform to specific body parts, e.g., the axilla. The embodiments of rotatable, movable, selectable alignment and conformable bore arrays have specifically been shown in the figures to have a single row of bores. It should be understood, however, that this is exemplary and that, in general, these bore arrays may range from a single row or column each consisting of at least one bore to a plurality of rows and/or columns of bores, i.e., the term array, in general, is defined to be a systematic arrangement of elements. Thus, useful arrays may also include arrangements other than distinct rows and columns.

Although embodiment lumens have generally been shown to be elongated, it should be understood that the teachings of the invention (and the definition herein of the term lumen) extend to lumens of other shapes and sizes that define a coordinate system, e.g., an elongated lumen between two end points could equivalently be replaced with small cylindrical lumens defining only the end points. It should also be understood that the term frame as used herein refers to an integral frame that defines elements such as lumens and bores as well as frames made up of a plurality of parts, some of which define these saint elements.

The preferred embodiments have shown Cartesian coordinate systems with orthogonal bore arrays arranged orthogonally with these systems. It should be apparent, however, that the teachings of the invention extend to any coordinate system, e.g., cartesian or polar, and any bore arrays that are arranged in operative association therewith, i.e., arranged to be directed at an imaging space represented by the coordinate system. Preferably, the bore arrays arc arranged to make it easy for operators to use the imaging determined lesion spacings in selecting appropriate guide bores.

Figure 37:
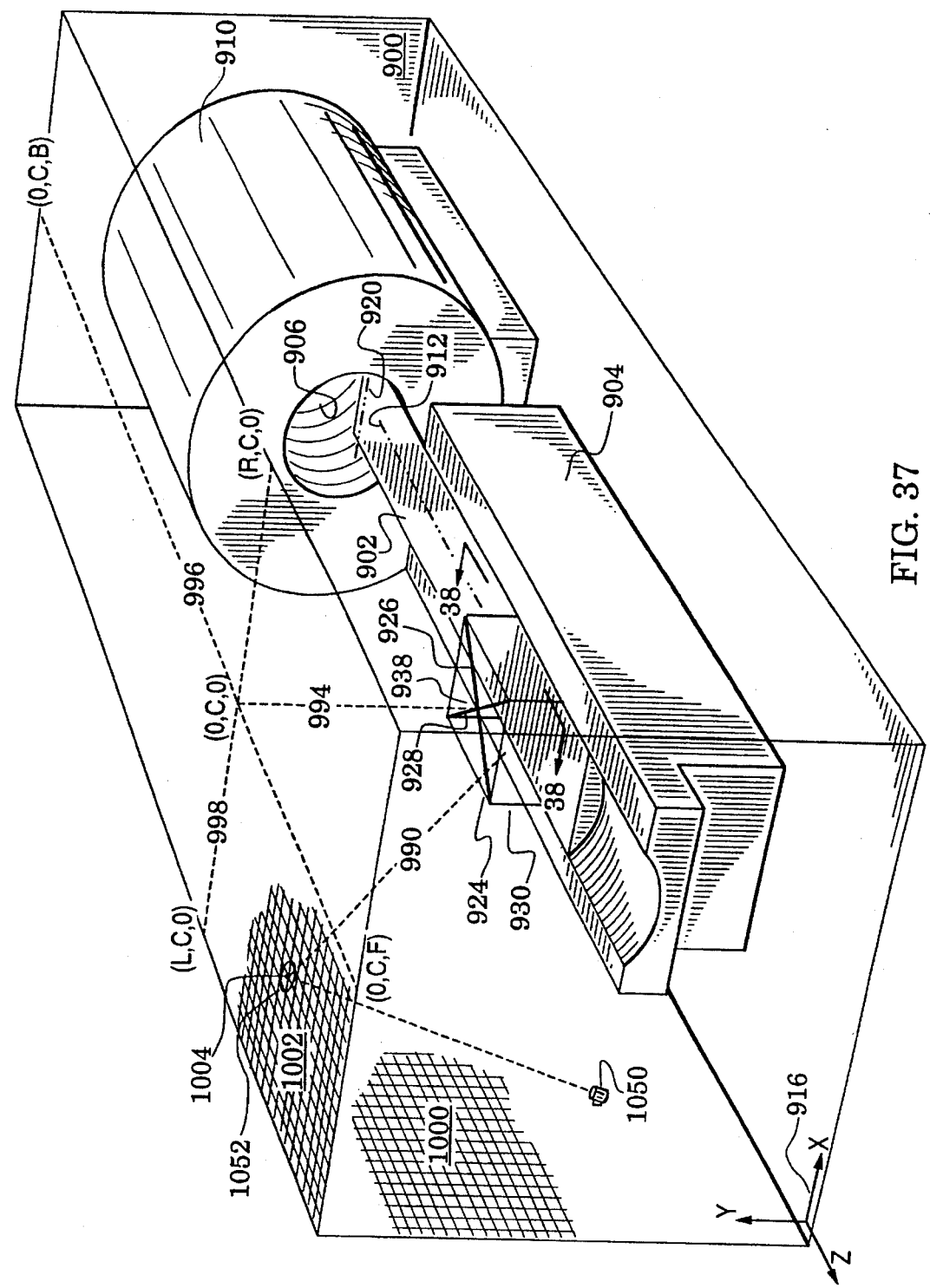
FIG. 37 is a perspective view of a preferred instrument guidance system in accordance with the present invention.

Attention is now directed to the localization methods and structure of FIGS. 37–43. FIG. 37 illustrates an orthogonal Computed Tomography (CT) imaging room 900 having an imaging table 902 which slides over a platform 904 and into the gantry 906 of the CT imager 910. The patient lies supine along the table's longitudinal axis 912 and is moved thereon progressively through the imager for scanning. Each imaged cross-section of the patient is done along a "scan plane". The scan plane generally varies in thickness between 1 and 10 millimeters and the interval between scan planes is usually equal to the scan plane thickness.

The position of the table along the longitudinal axis 912 is electronically referenced to the scan plane so that, for example, if an image slice (scan plane) is at the table position (and, therefore, patient position) 335 millimeters, the table and patient must be moved into the gantry 906 by 10 millimeters to be at position 345 millimeters and out of the gantry 906 by 12 millimeters to be at position 323 millimeters. Cartesian coordinate systems are conventionally used in imaging and one generally accepted convention, as indicated by the exemplary coordinate axes 916, defines the x axis to increase positively to the right wall, the y axis to increase positively to the ceiling and the z axis to increase towards the front wall. Obviously, any convention may be used as long as it is defined and followed throughout the imaging and localization procedure.

When a patient is scanned, each incremental movement of the table 902 is followed by a slice at the new scan plane to produce an image for that plane. The resulting image is annotated with the table position at the time the slice was taken. Consequently, if a lesion is demonstrated on a given slice, the table and patient may be moved back to the table position annotated on the image. This places the lesion once more in the scan plane.

Typically, the scan plane within the gantry is indicated by a laser called a line generator which illuminates a line along the table and patient. For example, if the line generator is turned on when the scan plane is through the patient's shoulders, a thin red line is displayed laterally over the surface of the shoulders. This laser line is schematically indicated by the broken line 920 within the gantry 906.

During needle biopsy procedures, a marker opaque to X-rays is typically placed within the lesion plane at a point selected for entry. With the marker in place, the table 902 is reset to the table position at which the lesion was imaged. The scan plane is reimaged so that the lesion (target point) and the marker (entry point) both appear on the computer display. A cursor may be placed over both points and the distance therebetween measured.

With the distance established, the radiologist will typically estimate the angular position (entry point—target point vector) required to insert the biopsy needle into the lesion. Alternatively, the angulation may be read from the computer and a stereotactic device employed to align the needle along the entry point—target point vector. The problem of determining distance and angulation becomes somewhat more complicated if the marker is placed on a transverse plane other than that containing the lesion. This may be the case, for example, in brain lesions where the entry point is commonly restrained to the crown of the head where the blood vessel network is less dense.

Many stereotactic devices are currently used in the instrument guidance art. For example, see descriptions in Stereotactic Neurosurgery, Galloway, R. et al., Critical Reviews in Biomedical Engineering, Volume 18, Issue 3, pages 184–205 and Stereotactic Instruments—Chapter 2 of Tumor Stereotaxis, Patrick J. Kelly M.D., W. B. Saunders Company, Philadelphia, 1991, the disclosures of which are hereby incorporated by reference. Most current stereotactic systems involve the use of elaborate guidance frames having different degrees of freedom. In the case of brain lesions, the frame is screwed or pinned to the head to prevent movement therebetween after which various movable arms, rings and arc quadrants are used to position the instrument along the entry point—target point vector. Such devices require time to set up and remove, add to patient distress and often (because of their size and complexity) reduce access to the patient. These devices must be mechanically calibrated which typically is associated with variable degrees of error.

A simpler and potentially more accurate localizer system, in accordance with the present invention, which allows almost unlimited access to the patient is schematically shown in FIGS. 37–41. Although the system may be used to localize lesions in any portion of the body, it is illustrated relative to a brain lesion. In FIG. 1, a fiducial plate 924 is placed on the scan table 902. The plate is made from an imaging transparent material and holds a pair of imaging visible fiducial rods 926, 928 in an x-shaped arrangement. The fiducial plate 924 is parallel with the x, z plane (orthogonal with the scan plane) and the rods 926, 928 are symmetrically arranged about the z axis (or table axis 912). Although the angle between the rods is arbitrary, the preferred embodiment is described with them in an orthogonal relationship. The fiducial plate 924 is held relative to the table by any conventional imaging transparent support structure 930.

The imaging visible rods 926, 928 are shown again in FIG. 38 which is a view along the plane 38—38 of FIG. 37 and in FIG. 39 which is a top plan view of FIG. 38. In these figures, a patient's head 934 is shown immobilized by a conformable thermoplastic mesh system 936 on the scan table 902 (the patient is typically placed along the table's longitudinal axis 912 with the feet adjacent the gantry 906 but is not shown in FIG. 3∂for illustration simplicity). The thermoplastic mesh system 936 is shaped to the head 934 and keeps it fixed relative to the table 902 throughout the imaging and localization procedure (mesh systems are available from various sources, e.g., Posicast™ thermoplastic material for radiation therapy masks manufactured by Sinmed by, Waddinxveen, The Netherlands). For illustration simplicity, only the fiducial rods 926, 928 are shown in FIG. In accordance with the preferred embodiment, the intersection 938 of the fiducial rods 926, 928 is assigned tile coordinates (0, 0, 0). The orientation of the coordinate system 916 is schematically indicated in FIGS. 37–41.

In FIGS. 38, 39 it is assumed that the patient has been scanned in the imager 910 and a lesion 940 observed when the plane 942 of the lesion was coplanar with the imaging scan plane in the gantry 906. An entry point for approach to the lesion 940 has been selected and an imaging visible marker 946 placed at this point on the patient's head 934. The table 902 is moved into the gantry 906 to form an image when the plane 948 of the marker 946 is coplanar with the imaging scan plane. The two resulting scan plane images are respectively shown in FIGS. 40 and 41 rotated rightward 90 degrees from their standard appearance on the computer monitor 950 for the purposes of these illustrations.

In FIG. 40, the elliptical cross sections 956, 958 of the fiducial rods 926, 928 along the scan plane are displayed along with the cross section of the lesion 940. The fiducial rod cross sections 956, 958 and lesion cross section 940 lie on projection lines 960, 962 and 964, respectively and their horizontal spacing results from their vertical spacing in FIG. 38 (the projection lines are for present descriptive purposes only). In a similar manner, the fiducial rod cross sections 966, 968 and marker cross section 946 are displayed in FIG. 41 where the rod cross sections and marker cross section lie on projection lines 970, 972 and 974 respectively.

In FIG. 40, the computer cursor can be placed on the rod cross sections and the lesion to determine the lesion coordinates. It is apparent that the y axis coordinate y(t) of the lesion is the spacing 980 between the plane of the rod cross sections 956, 958 and the lesion 940 and the x axis coordinate x(t) is the spacing 982 between the lesion and a perpendicular line 984 that bisects the spacing 986 between the rod cross sections.

Finally, the z axis coordinate z(t) is one half of the spacing 986. This follows because the fiducial rods 926, 928 are orthogonal in FIG. 39 and form a right isosceles triangle with the lesion plane (942 in FIG. 38). As the lesion plane 942 moves away from the intersection 938, its spacing therefrom is necessarily twice the spacing between the intersection of the plane and the fiducial rods (from the trigonometric relationships of right isosceles triangles). If the fiducial rods are arranged at an angle other than 90 degrees, the appropriate geometric relationship using the rule of similar triangles would be substituted for that just described.

Thus, the lesion (target) coordinates x(t), y(t), z(t) can be measured in terms of an imaging space by cursor placings on the computer monitor. In a similar manner the entry point coordinates x(e), y(e), z(e) are determined from the computer monitor. As shown in FIGS. 38, 37, these two points establish the desired entry point—target point line 990 where this line is now determined in terms of the imaging space defined by the coordinate system which has an origin at the fiducial rod intersection 938. Generally, this intersection could have any assigned coordinate in the coordinate system, but in the preferred embodiment being described it is assigned the origin for simplification of understanding and manipulation. A mathematical definition of this line is: for Pe[x(e), y(e), z(e)] and Pt[x(t), y(t), z(t)]:

$$[x-x(e)]/[x(t)-x(e)]=[y-y(e)]/[y(t)-y(e)]=[z-z(e)]/[z(t)-z(e)]$$

Thus, in accordance with a first feature of the invention, the coordinates of the target point and the entry point (and hence, the entry point—target point line 990) are established in terms of an imaging space that has its origin (or other established coordinate) at the intersection of two fiduciary elements that are arranged at an angle therebetween. The imaging visible, angled fiduciary elements (rods 926, 928) provide all the information necessary for establishing the entry point—target point line 990.

The intersection of the fiduciary rods is embedded in a coordinate system that radiates outward in all directions. In accordance with a second feature of the invention, selected coordinate sets of this imaging space coordinate system are manifested, i.e., made evident. The intersection of the entry point—target point vector 990 with these manifested coordinate sets is then available to aid in aligning a medical instrument with the line. In particular, with the aid of the manifested imaging space coordinate sets, a retrograde point lying on the entry point—target point line 990 is determined wherein the entry point lies between the retrograde point and the target point, i.e., the retrograde point, entry point and lesion are substantially colinear.

The establishment of a third point, the retrograde point, provides, with the entry point, all the information needed for guidance of the medical instrument to the lesion thus obviating the need for an internally or self-referenced stereotactic frame. As mentioned above, such stereotactic guidance frames typically must be rigidly attached to the head (in the case of cranial lesions) requiring surgical intrusion into the skull and also intruding into the operating space of the surgeon. In the present system, the fiducial rods 926, 928 and their support 930 may be removed after the entry point—target point line 990 is established to provide almost unlimited patient access.

Attention is now directed to the manifestation of selected coordinate sets of the imaging space in the preferred embodiment illustrated in FIG. 37. The table 902 and attached fiducial rods 926, 928 are set at a reference position in the room. FIG. 37 illustrates the table set at the reference position (this could, for example, be table position 0) from which all points in the room are now defined by the same imaging space coordinate system.

A laser may be positioned at the (0,C,0) point of the ceiling and directed downward. When this laser strikes the intersection 938, the table is properly reset to the room's coordinates. Of course, the laser could, instead, be directed upward from the intersection 938 to strike the ceiling. Alternatively, a plumb line could be used to properly register the table 902 and fiducial rods 926, 928 with the room 900.

In FIG. 37, the broken line 994 leads upward from the intersection 938 to intersect the imaging room ceiling at (0,C,0), i.e., a distance C above the origin. All points on the ceiling thus lie in the (x,C,z) plane. The broken line 996 parallel to the z axis intersects the imaging walls at (0,C,F) and (0,C,B) while the broken line 998 parallel to the x axis intersects the imaging room walls at (L,C,0) and (R,C,0) where F, B, L and R are floor or ceiling dimensions from the origin to the respective walls. Thus, the left wall lies in the (L,y,z) plane, the front wall lies in the (x,y,F) plane and so on.

Any selected coordinate sets of this imaging space coordinate system may be made manifest for establishing the retrograde point. There are many equivalent ways in the art for manifesting these sets. In the preferred embodiment shown in FIG. 37, an indicia in the form of a grid 1000 that is defined on one wall and a grid 1002 that is defined on the ceiling. These grids may be partial or continued over the entire inner walls and ceilings of the imaging room. In other embodiments of the invention, point sets of the coordinate system may be made manifest by other means. For example, tape marked with grid lines may be moved along the walls and/or ceiling. Alternatively, combinations of lasers may be used to cast coordinate lines in selected areas or surfaces of the room.

A computer is particularly useful in determining the retrograde point on the manifested coordinate sets. With the spatial relationship of the manifested coordinate sets stored in the computer's memory, it can easily define the retrograde point using the mathematical definition of line 990 by solving this equation for the values of P[x(e), y(e), z(e)], P[x(t), y(t), z(t)] and each of the values L, R, F, B and C. The retrograde point is the mathematical "pierce point" of the line with the manifest set. In FIG. 37, the retrograde point is the intersection or "pierce point" 1004 of the entry point—target point line 990 with the ceiling plane.

In accordance with a third feature of the invention, antegrade and retrograde lasers are associated with the medical instrument to guide it along the entry point—target point line 990. Accordingly, a medical instrument insertion device 1010 is schematically illustrated in FIG. 42 supporting a medical instrument 1011 having a shaft 1014 within a needle guide 1016. It further has provisions for positioning an antegrade laser 1018 and a retrograde laser 1020 whose beams are respectively indicated by broken lines 1022, 1024.

The antegrade and retrograde lasers 1018 and 1020 and needle guide 1016 are coaxially positioned on an instrument holder 1030 having a first rod 1032 rotatably mounted on a second rod 1034 which is slidably mounted in a stand 1036. The elements of the instrument are interconnected with clamps 1038.

The antegrade laser beam 1022 is directed through the bore of the needle guide 1016 during alignment of the medical instrument insertion device 1010 proximate to the entry point (946 in FIGS. 38, 39). The shaft 1014 would then typically be inserted through the guide 1016 as shown. Alternatively, the medical instrument 1011 could be removed, the beam 1022 of the antegrade laser 1018 used to illuminate the entry point and the medical instrument 1011 inserted with a "freehand technique".

The mechanical details of the medical instrument insertion device are not essential to the invention as long as they position the antegrade and retrograde lasers 1018, 1020 substantially coaxial with the treatment axis of the medical instrument insertion devive 1010 and as long as the medical instrument device 1010 is rigidly stabilized.

If the medical instrument insertion device 1010 is oriented with the antegrade laser 1018 illuminating the entry point 946 shown in FIGS. 38, 39 and the retrograde laser 1020 illuminating the retrograde point 1004 of FIG. 37, then the instrument 1010 treatment axis is coaxial with the entry point—target point line 990. Finally, if the instrument tip 1040 is placed on the entry point 946, the depth of needle insertion to reach the lesion 940 is given by the equation of $d=\{[x(t)-x(e)]^2+[y(t)-y(e)]^2+[z(t)-z(e)]^2\}^{1/2}$ (where t and e indicate target and entry point), i.e., the solution for one side of a three dimensional triangle given the other two sides. Alternatively, the tip 1040 may be placed at the entry point 940 and only the retrograde laser used to illuminate the retrograde point 1004.

The retrograde laser may be carried by the hub of the needle itself which may permit "freehand" stereotactic localization. In this embodiment, the needle tip touches the entry point as the retrograde laser illuminates the retrograde point. Alternatively, the antegrade laser may illuminate the center of the needle hub as the needle tip touches the insertion point. This method also allows freehand localization. The retrograde and antegrade lasers are aligned and immobilized colinear with the needle insertion vector.

The support details of the medical instrument insertion device 1010 may be replaced with any of the well known instrument holders in the art, e.g., see Lunsford, et al., Probe holder for Stereotactic Surgery in the CT Scanner, Acta Neurochirurgica, 69, 297–304, 1983, the disclosure of which is hereby incorporated by reference. In accordance with the present invention, these holders may be used for mounting the antegrade and retrograde lasers as well as for stabilization of the instrument as it is guided by the lasers.

Another embodiment of the invention includes a laser 1050 configured to direct an antegrade beam along the line 990 in FIG. 37 from a selected retrograde point 1004. This antegrade beam could be used to illuminate the entry point (946 in FIG. 38). The laser 1050 is mounted on a wall of the room 900 and is directed at an apparatus mounted at the retrograde point, e.g., a mirror represented by the oval line 1052, which is employed to cast the laser beam from the retrograde point 1004 along the line 990 to the entry point. Alternatively, the laser, represented by the oval line 1052, is mounted at the retrograde point and is directed to cast the laser beam along the line 990 to the entry point.

From the foregoing it should now be recognized that embodiments of a medical instrument guidance system have been disclosed herein that determine an imaging space retrograde point for use in instrument guidance. Methods and apparatus in accordance with the present invention provide instrument guidance to lesions without requiring apparatus mounted to the head of to the patient that restricts surgeon access thereto. The accuracy of this instrument is not affected by mechanical calibration of a stereotactic frame which typically is imperfect. Accuracy may be increased by enlarging the dimensions of the manifest coordinate system. Although the embodiments were described relative to a computed tomography imaging modality, the teachings of the invention may equivalently be used with other imaging modalities and equipment therefor, e.g., magnetic resonance imaging (MRI), by those skilled in the art. All embodiments are applicable to non-orthogonal scan rooms and/or scan planes. The manifest coordinate system may include the scanner face, a positionable booth or a surface attached to a mechanical arm among other conceivable structures.

The preferred embodiments of the invention described herein are exemplary and numerous modifications, dimensional variations and rearrangements can be readily envisioned to achieve an equivalent result, all of which are intended to be embraced within the scope of the appended claims.

What is claimed is:

1. A method for guiding an instrument tip to a target point identified in a patient via an imaging modality, comprising the steps of:

establishing an imaging space coordinate system;

selecting an entry point;

placing an imaging visible marker at said entry point;

imaging said target point and said entry point to determine the imaging space coordinates thereof;

determining the coordinates of a retrograde point that lies on a line defined by said entry point coordinates and said target point coordinates wherein said entry point is between said retrograde point and said target point; and, providing a retrograde laser having a retrograde laser beam and a medical instrument having said tip;

causing said retrograde laser beam to be directed along said line to illuminate said retrograde point; and, guiding said instrument along said line by keeping said retrograde beam on said retrograde point to position said instrument tip proximate to said target point.

2. The method of claim 1 wherein said imaging step further includes the steps of:

disposing at least one imaging visible fiduciary member in a spaced relationship with said target point; and, employing the image of said fiduciary member to determine said coordinates.

3. The method of claim 1 wherein said determining step further includes the steps of:

manifesting a set of imaging space coordinates; and, finding the intersection of said line with said coordinate set.

4. The method of claim 1 further including the steps of:

providing an antegrade laser having an antegrade laser beam;

directing said antegrade laser beam along said line; and, illuminating said entry point with said antegrade laser beam.

5. The method of claim 4 wherein said directing said antegrade laser beam step includes originating said antegrade laser beam from said instrument.

6. The method of claim 4 wherein said medical instrument further includes an end spaced from said instrument tip and said guiding step includes the step of illuminating said end antegrade laser beam as said tip is positioned at said entry point and moved along said line to position said tip proximate to said target point by freehand technique.

7. The method of claim 1 further including the step of providing a thermoplastic mesh for immobilizing a body part containing said target point.

8. A method of guiding an instrument tip to a target point identified in a patient via an imaging modality, comprising the steps of:

establishing an imaging space coordinate system;

selecting an entry point;

placing an imaging visible marker at said entry point;

imaging said target point and said entry point to determine the imaging space coordinates thereof;

determining the coordinates of a retrograde point that lies on a line defined by said entry point coordinates and said target point coordinates wherein said entry point is between said retrograde point and said target point;

providing an antegrade laser having an antegrade laser beam and a medical instrument having a tip;

causing said antegrade laser beam to be directed from said retrograde point along said line to illuminate said entry point; and, guiding said instrument along said antegrade beam to position said instrument tip proximate to said target point.

9. The method of claim 8 wherein said imaging step further includes the steps of:

disposing at least one imaging visible fiduciary member in a spaced relationship with said target point; and, employing the image of said fiduciary member to determine said line.

10. The method of claim 8 wherein said medical instrument further includes an end spaced from said instrument tip and said guiding step includes the step of illuminating said end with said antegrade laser beam as said tip is positioned at said entry point and moved along said line to position said tip proximate to said target point by freehand technique.

11. The method of claim 8 further including the step of providing a thermoplastic mesh for immobilizing a body part containing said target point.

12. Apparatus for use with a medical imaging system for guiding an instrument tip to a target point in a patient via a selected entry point on a patient, the apparatus comprising:

indicia manifesting a selected coordinate set spaced from the patient;

means for determining the imaging space coordinates of the entry point and target point, defining a line therebetween, and locating a retrograde point on said line at the intersection of said line with said indicia wherein said entry point is between said retrograde point and said target point;

means for manifesting said retrograde point on said indicia;

a medical instrument having a tip; and, means for utilizing said retrograde point for guiding said instrument along said line for positioning said tip proximate to said target point including a retrograde laser for providing a retrograde laser beam along said line for illuminating said retrograde point.

13. Apparatus of claim 12 wherein said determining means includes at least one imaging visible fiduciary member for placement in a spaced relationship with the target point.

14. Apparatus of claim 12 and further including an antegrade laser for providing an antegrade laser beam directed along said line for illuminating said entry point.

15. Apparatus of claim 12 wherein said indicia for manifesting a selected coordinate set includes a room having a least one surface and a grid on said at least one surface.

16. Apparatus of claim 12 wherein said determining means includes a computer.

17. Apparatus for use with a medical imaging system for guiding an instrument tip to a target point in a patient via a selected entry point on a patient, the apparatus comprising:

indicia manifesting a selected coordinate set spaced from the patient;

means for determining the imaging space coordinates of the entry point and target point, defining a line therebetween, and locating a retrograde point on said line at the intersection of said line with said indicia wherein said entry point is between said retrograde point and said target point;

means for manifesting said retrograde point on said indicia;

a medical instrument having a tip; and, means for utilizing said retrograde point for guiding said instrument along said line for positioning said tip proximate to said target point including an antegrade laser for providing an antegrade laser beam along said line for illuminating said entry point.

18. Apparatus of claim 17 wherein said means for utilizing said retrograde point includes said antegrade laser coupled to said manifest retrograde point.

19. Apparatus of claim 17 wherein said means for utilizing said retrograde point includes:

said antegrade laser spaced from said manifest retrograde point; and, a mirror coupled to said manifest retrograde point for directing said antegrade laser beam along said line to said entry point.

* * * * *